(12) United States Patent
Pollack et al.

(10) Patent No.: US 7,306,632 B2
(45) Date of Patent: Dec. 11, 2007

(54) LEAVE-IN COLOR CONDITIONER

(75) Inventors: George Pollack, Fair Lawn, NJ (US); Robert Sobel, Santa Fe, NM (US)

(73) Assignee: HairMarker LLC, Santa Fe, NM (US)

( * ) Notice: Subject to any disclaimer, the term of this patent is extended or adjusted under 35 U.S.C. 154(b) by 340 days.

(21) Appl. No.: 11/071,022

(22) Filed: Mar. 3, 2005

(65) Prior Publication Data

US 2005/0198746 A1    Sep. 15, 2005

(51) Int. Cl.
*A61K 7/13*    (2006.01)

(52) U.S. Cl. .................. 8/405; 8/455; 8/463; 8/488; 8/512; 8/514; 8/552; 8/553; 8/581

(58) Field of Classification Search .................. 8/405, 8/455, 463, 488, 512, 514, 552, 553, 581
See application file for complete search history.

(56) References Cited

U.S. PATENT DOCUMENTS

| | | | |
|---|---|---|---|
| 4,153,065 A | 5/1979 | Lang | |
| 4,699,625 A * | 10/1987 | Jenkins | 8/532 |
| 5,964,226 A | 10/1999 | Sobel | |
| 6,379,400 B1 | 4/2002 | Braun et al. | |
| 7,087,095 B2 * | 8/2006 | Pollack | 8/405 |

FOREIGN PATENT DOCUMENTS

| | | |
|---|---|---|
| DE | 196 51 482 C1 | 4/1998 |
| WO | WO 97/44002 | 11/1997 |

* cited by examiner

*Primary Examiner*—Eisa Elhilo
(74) *Attorney, Agent, or Firm*—Duane A. Stewart, III; Buchanan Ingersoll & Rooney PC

(57) ABSTRACT

The invention is directed to novel hair dye compositions, novel leave-in conditioners, and novel leave-in conditioners with a hair coloring effect. Hair dye compositions, leave-in conditioners, and leave-in conditioners with hair coloring effect may include a styrene/vinylpyrrolidone copolymer emulsion.

16 Claims, No Drawings

US 7,306,632 B2

LEAVE-IN COLOR CONDITIONER

CLAIM FOR BENEFIT OF PRIORITY

This application claims priority of pending U.S. patent application Ser. No. 09/568,830, "Hair Coloring Composition and Method," filed on May 11, 2000, and pending U.S. patent application Ser. No. 10/215,303, "Hair Coloring Composition and Method," filed on Aug. 6, 2002. All applications share a common inventor, George Pollack. The second inventor on this application, Robert Sobel, is not an inventor on either of the prior applications. Both priority documents are incorporated by reference as if fully rewritten herein.

FIELD OF INVENTION

The present invention relates to hair conditioning compositions, hair dyeing compositions, and combined hair conditioning and dyeing compositions.

BACKGROUND

Many compositions for dyeing human hair are known. Often hair dyeing involves applying a dye composition and fixing it by oxidation using peroxide or the like. The dyes used in those procedures are known as "permanent" or "oxidative" hair dyes. Their effects may last for a number of weeks or months. Other hair dyes may be applied without oxidation. These dyes are known as "semi-permanent" dyes. Their effects may last for about 6 to about 12 weeks.

Compositions for conditioning hair have also been reported. For example, U.S. Pat. No. 4,964,874, to Saphakkul, reports an aqueous hair conditioner product comprising a cationic surfactant, a fatty alcohol having an alkyl group with from 8 to 22 carbon atoms, a basic dye, and a neutral dye. Saphakkul reports that the cationic surfactant is present in a disperse lamellar liquid crystal phase with a certain weight ratio.

It is an object of the invention to provide a dye composition for temporary or semi-permanent use. It is a further object of the invention to provide a hair conditioner that does not need to be rinsed out of hair immediately following application. It is a still further object of the invention to provide a hair conditioner and dye composition that does not need to be rinsed out of hair immediately following application and that imparts a tint or color to conditioned hair. Of course, the scope of the invention is defined by the claims, and the claims should not be limited by reference to the objects of the invention unless specifically stated therein.

BRIEF DESCRIPTION OF THE INVENTION

A hair dyeing composition of the present invention generally comprises an acid or basic temporary dye or solvent-type temporary dye. They are generally acid dyes or solvent dyes. Generally the various FD&C and D&C dyes fall into this category of dyes that are useful in accordance with the present invention. Dyes that are useful in accordance with the present invention may be categorized in the Color Index (C.I.) under their own C.I. numbers. Some dye compositions of the invention are capable of capillary flow in solution; however, in some aspects of the invention dye compositions may be created that are incapable of capillary flow or have poor capillary flow.

Such dye compositions may be free of or contain a low concentration of foaming agents such as surfactants or detergents. They may have a controlled, nearly free-flowing viscosity. Their viscosity may be in the range of from about 10 to about 200 cps to be nearly but not quite free flowing and yet not drip or cause a buildup on the hair. In other aspects of the invention, a controlled viscosity is not required. The dye composition may be soluble in water and/or in alcohol, and may be dissolved in a liquid vehicle that may have a controlled vapor pressure for a predetermined rate of evaporation, i.e. a controlled rate of drying. Dye compositions of the invention may include a styrene/vinylpyrrolidone copolymer emulsion commercially known in the United States as Polectron 430 (International Specialty Products) and in Europe and Asia as Antara 430 (International Specialty Products).

Dye compositions of the present invention can optionally also contain a clear polymeric dye-shield anti-ruboff component to prevent the transfer of the applied color from the hair to surfaces such as pillows, clothes, etc., such as a polymer of vinyl acetate and of vinyl pyrrolidone, or a copolymer thereof which has been found to be particularly effective for that purpose. Although applicant does not wish to be bound by theory, it is believed that the Polectron® 430 (International Specialty Products) also provides an anti-ruboff effect. Dye compositions may include other optional ingredients, including but not limited to sunscreens, conditioning silicones, such as Dow Corning 939 (Dow Corning) or Dow Corning 949 (Dow Corning) (amodimethicone), and other substances that may be known to those skilled in the art.

In another aspect the invention includes a novel hair conditioner (a "leave-in conditioner") that, unlike conventionally available conditioners, may provide benefits when allowed to remain in the hair instead of being rinsed out of the hair shortly following application. Such a leave-in conditioner may include a cationic holding polymer, cationic wheat protein, cationic conditioning agent from a long-chain fatty acid, cationic cellulosic polymer, silicone, glycerin, and ultraviolet absorbers (to prevent, for example, sunlight damage, color loss, or hair breakdown). A "long chain" fatty acid may be, for example, a fatty acid with a length of C8-C22.

In a further aspect the invention includes a novel leave-in color conditioner that includes a dyeing composition combined with a leave-in conditioner composition to impart a lasting tint to hair. Such a tint may last until the user's next shampoo. The combination leave-in conditioner and dye product (the "leave-in color conditioner") may combine a novel dye composition of the invention with a novel leave-in conditioner of the invention.

DETAILED DESCRIPTION

I. Dye Compositions Including Polectron® 430 (International Specialty Products)

Novel hair dyeing compositions of the present invention may comprise one or more FD&C dyes, D&C dyes, Ext. D&C Dyes, cationic dyes, anionic dyes, or other dyes as may be known by those skilled in the art. "FD&C dyes," "D&C dyes," and "Ext. D&C Dyes" refers to those dyes approved (or not requiring approval) for use in food, drugs, and cosmetics or for use in drugs and cosmetics by the United States Food and Drug Administration. Those dyes are listed, for example, in 21 C.F.R. §§ 73-74 (April 2004), which is incorporated by reference as if fully rewritten herein. The dyes may be present in individual concentrations of about 0.10 to about 5.0% wt. based on the composition, and for more intense colors, preferably between about 0.10 to about 3.0% wt.

FD&C dyes, D&C dyes, and Ext. D&C dyes suitable for use in the invention are set forth in Appendix 1 at the conclusion of this application, as excerpted from the United States Code of Federal Regulations Chapter 21, Part 74, with additions and deletions as needed.

A hair dyeing composition of the invention may contain up to about 0.20% wt. of a conditioning, hydrolyzed wheat protein, sold by the Croda Company under the trade designation Tritisol®. A hair dyeing composition may contain up to about 0.1% of a shine-contributing silicone, such as the silicone sold by Dow Corning Corp. under the trade designation Silicon 193 (a dimethicone copolyol). The Tritisol hydrolyzed wheat protein is a nonionic compound and does not interfere with anionic, cationic, or nonionic dyes, and does not cause any precipitation or foaming.

The Polectron® 430 (International Specialty Products) copolymer emulsion can be suitably employed at a concentration of between about 10% wt. to about 50% wt., most suitably about 20% wt. It produces more vivid colors with dyes of the present invention, and delivers a truer result. The balance of a dye composition of the invention may be the solvent portion of the dye composition.

The total solvent (e.g. water plus volatile solvent) can be up to about 80% wt. of the dye composition to leave some room for the up to about 20% Polectron® 430 (International Specialty Products) 430 polymer additive. Butyl cellosolve or alcohol proportion in the vehicle can be varied up to about 50% of the solvent, with a lower percentage being preferred, with a proportionally lower concentration of water, when a higher rate of evaporation is desired. Up to about 5.0% wt. of propylene glycol, and up to about 20% wt. ethyl alcohol may also be included. The appropriate proportions of water and the more volatile solvent can be determined by routine experimentation (with the benefit of the teachings in this specification) to obtain the desired evaporation rate. In general, deionized water may be used in an amount as desired to balance of the composition to a total of 100%. Level application of dyes of the invention can be promoted by the use of an alcohol solvent system. An alcohol solvent system may contain, but is not limited to ethyl alcohol, isopropyl alcohol or a butyl alcohol, including but not limited to tert-butyl alcohol, butylene glycol, 2-butanol, or butoxyethanol (butyl cellosolve).

In one aspect of the invention, dyes including Polectron® 430 (International Specialty Products) are capable of instantaneous application upon touching the hair and should not drip. The dyes should be capable of penetrating the cuticle of the hair in a level fashion without leaving an undesirable coating. Dye compositions may be non-foaming and should be at least somewhat quick drying.

Dye compositions of the invention may impart a temporary or semi-permanent color. As recognized by those skilled in the art, much of the staying power of a given dye composition will be dependent on the nature of the dye used in the composition and the pH at which the composition is used. For instance, FD&C, D&C and Ext. D&C dyes that are applied in a composition with an acidic pH may impart a temporary color, while cationic or anionic dyes may impart a semipermanent color when used with the Polectron® emulsion in a dye composition of the invention.

When used with an applicator apparatus the composition may have a sufficiently low viscosity so that the composition flows easily from the applicator to the hair surfaces contacted thereby, and should have a suitable acid pH to allow the desired degree permanence on the hair. Of course, one skilled in the art may, with the benefit of this disclosure, adjust the viscosity so that a particular applicator may be used without the use and accumulation of too much dye composition on the hair or in the surrounding environment.

Those skilled in the art will recognize, with the benefit of this disclosure, that optimal pH of a dye composition of the invention containing FD&C, Ext. D&C and/or D&C dyes may be, for example, between about 5.0 to about 7.0. It has been found that the composition for hair coloring should be at a pH from about 6 to about 6.5 for best coloring of the hair using FD&C, D&C, and/or Ext D&C dyes, however, the most suitable pH will also depend on the identity of the dye and its host substantivity, as will be readily known to the skilled hair colorist. For instance, when a dye composition of the invention includes a cationic semipermanent dye, such as, for example, but not limited to an azo dye or an anthroquinone dye, an alkaline pH is preferred. The alkaline pH may be, but is not limited to, a pH between about 7.5 to about 9.0, a pH between about 8.0 to about 8.5, or a pH of about 8.5.

In one aspect of the present invention the dyes used are FD&C dyes, Ext. D&C dyes, and/or D&C dyes. Suitable dyes are generally water and alcohol soluble and are safe for use on human hair. The ratio of water and alcohol or other volatile solvent can be varied in the vehicle of the hair dye composition to obtain a predetermined rate of evaporation thereof.

In another aspect of the invention suitable dyes include one or more FD&C, Ext. D&C, and D&C dyes. These dyes are suitably used by themselves or mixed with other FD&C and D&C dyes and/or other non-FD&C and D&C dyes. These FD&C and D&C dyes require no preliminary patch test, and are more vivid and deliver truer colors to hair. However, if the addition of any other type of hair dye is desired, then a patch test should be carried out on a skin patch for about 48 hours prior to use. Other suitable dyes may include azo dyes, xanthene dyes, triphenylmethane dyes, anthroquinone dyes, pyrene dyes, pyrazole dyes, monoazo dyes, fluoran dyes, disazo dyes, and nitro dyes.

The dyes may moreover be capable of being instantly deposited on the hair. They allow for repeated touching to the hair with increased coverage upon each application. They penetrate the hair shaft leaving a clean, non-messy level of color molecules on the hair. No unsightly mess is left on the hair or scalp on drying.

Dye compositions of the present invention can suitably contain a vinylpyrrolidone/styrene copolymer nonionic emulsion, such as that sold under the trademark Polectron® 430 by International Specialty Products, Inc. This is a fluid, milky white emulsion with a solids content of about 40% wt. Its solids content has a particle size under about 0.5 microns. It assists in the even distribution and prolonged suspension and improved stability of the colors. It contributes to a more even flow of colors and their application and it helps to prevent dye transfer.

An optional protective ruboff shield component may be included to provide against ruboff of the color to objects coming into contact with dyed hair, e.g., pillow cases, clothing, etc. The polymeric ruboff shield should not interfere with the coloring process. The polymer used in the present composition is compatible with the hair while forming a ruboff shield that surrounds each hair shaft and is gradually removed upon each subsequent shampooing. Polyvinylpyrrolidone alone or copolymers of vinyl acetate and vinylpyrrolidone monomers, or mixtures, such as is sold by International Specialty Chemicals, Corp. under the trade designation PVP/VA E635, are particularly effective to serve this purpose, because they are not tacky and do not interfere with the free capillary flow of the dye liquids. Generally 50% solutions of these copolymers are sold by International Specialty Products Corp., and by BASF. Other polymers may be used, particularly nonionic polymers, and many others can be identified by reasonable experimentation conducted with the benefit of this disclosure.

The viscosity of the composition to be used is important to be free-flowing and yet not drip or cause a build-up on the hair. Viscosity may be adjusted through use of a thickener. A thickener such as a carbomer or a cellulose can be used to prevent too rapid a runoff from an applicator. A viscosity in the range of about 10 cps to about 200 cps may be used, more suitably between 10 and 100 cps.

II. Leave-In Conditioner

In another aspect the invention includes a leave-in conditioner. The leave-in conditioner may be wetted and restyled, with a long-lasting shine.

A leave-in conditioner of the invention may include, for example, but is not limited to, cationic holding polymer, cationic wheat protein, cationic conditioning agent from a long chain fatty acid, cationic cellulosic polymer, silicone, glycerin, and ultraviolet absorbers. Cationic holding polymers that may be used in the invention include but are not limited to the polymer known as Gafquat™ 755N (International Specialty Products), which is quaternized copolymer of vinylpyrrolidone and dimethyl aminoethylmethacrylate. Cationic conditioning agents may be selected from, for example, olealkonium chloride. The conditioning agent panthenol may also be included. Cationic cellulosic polymers for use in the invention include the polymer commercially sold Ucare® polymer JR (Amerchol). Ultraviolet absorbers included in the invention may include, for example, Incroquat UV 283 (Croda, Inc.), and benzophenone-4. Silicone that may be used includes the variety sold by Dow Corning under the trade designation Dow Corning 193. Olealkonium chloride may also act as a clarifying agent. At least one preservative may also be included in the leave-in conditioner. For example, the leave-in conditioner may include DMDM Hydantoin. An antioxidant such as the Croda product Heligenol may also be included. The composition may include one or more beneficial extracts. These extracts may be, for example, lemon extract, chamomile extract, rosehips extract, or green tea extract.

The below ranges in Table 1 are included by way of example only and should not be construed to limit the claims. Values given are approximate.

TABLE 1

Examplary Leave-In Conditioner

| Ingredient | % by weight |
| --- | --- |
| Deionized Water (qs) | Balance to 100% |
| Benzophenone-4 (UV absorber) | 0.05 |
| Natrosol (Hercules/Aqualon) | 0.0-.5% |
| Ucare ® Polymer JR (Amerchol) | 0.3-1.0 |
| Cationic wheat protein | 0.1-1.0 |
| Olealkonium Chloride | 0.4-1.0 |
| Gafquat 755 International Specialty Products | 2.0-5.0 |
| Dow Corning 193 | 0.2-1.0 |
| Incroquat UV 283 (Croda) | 0.0-2.0 |
| Heliogenol (Croda) | 0.0-1.0 |
| DMDM Hydantoin | 0.4-0.7 |
| Panthenol | 0.05-0.10 |
| Glycerin | 1.0-8.5 |
| Lemon Extract | 0.00-0.1 |
| Chamomile Extract | 0.00-0.1 |

TABLE 1-continued

Examplary Leave-In Conditioner

| Ingredient | % by weight |
| --- | --- |
| Rosehips Extract | 0.00-0.1 |
| Green Tea Extract | 0.00-0.1 |

III. Leave-In Color Conditioner

In a further aspect the invention includes a leave-in color conditioner. A leave-in color conditioner of the invention may be pre-mixed, or it may be sold as a kit.

A leave-in color conditioner of the invention may include, for example, a leave-in conditioner as described in Part II of this disclosure, and one or more hair dyes. The dyes may be, for example, but are not limited to cationic dyes, azo dyes, diphenyldiamine dyes, quinone-imine dyes containing a quaternary ammonium group, and direct nitro dyes. In some aspects of the invention, anionic dyes are excluded. In other aspects of the invention, the composition is substantially free of anionic dyes. By "substantially free" it is meant that anionic dye is present in an amount less than about 0.5% wt.

The hair coloring composition for use in a leave-in color conditioner of the invention may have a formula as shown below. The components are grouped in Phases A, B and C to correspond to the process steps used in their manufacture.

| Hair Coloring Formula | Percent wt |
| --- | --- |
| Phase A | |
| Deionized Water | Balance of composition to 100% |
| PVP/VA or E735 (polymer) | 2.0-4.0 |
| Crotein Hydrotriticum QM (Croda) | 0.05-0.5 |
| Dow Corning Silicone 193, 939, and/or 949 (for shine) | 0.00-0.5 |
| Triethanolamine (pH adjuster) qs to pH 8.5 | |
| Phase B - Cationic Dyes (May be included in listed amounts together or in the alternative | |
| Deionized Water | Balance to 100% |
| Arianor Steel Blue (Warner-Jenkinson) | 0.05-2.0 |
| Arianor Madder Red (Warner-Jenkinson) | 0.1-1.0 |
| Arianor Straw Yellow (Warner-Jenkinson) | 0.05-1.0 |
| Arianor Crazy Gold (Warner-Jenkinson) | 0.05-0.7 |
| Arianor Flame Red (Warner-Jenkinson) | 0.05-0.7 |
| Arianor Orange (Warner-Jenkinson) | 0.05-0.7 |
| Arianor Mahogany Brown (Warner-Jenkinson) | 0.05-1.0 |
| Arianor Sienna Brown (Warner-Jenkinson) | 0.05-1.0 |
| Lowacryl Violet 4 (Lowenstein) | 0.05-0.3 |
| Lowacryl Violet 14 (Lowenstein) | 0.05-0.3 |
| Lowacryl Red 2 (Lowenstein) | 0.05-0.3 |
| Phase C | |
| Ethyl Alcohol | 10.0-20.0 |
| Phase D | |
| Polectron ® 430 by International Specialty Products | 0.1-20.0 |
| Phase E | |
| Fragrance | 0.05-0.2 |

The above formula will yield the complete range of colors needed for dyeing hair of all types of shades. If the shade is too weak it will be known to the colorist to increase the color in small increments until the desired shade is reached. If the color is too strong, a base without the color can be added until the color is the desired shade. A final pH for.

A leave-in color conditioner may have a number of advantages. For instance, it may yield a bright color result that is sufficient to tone down grey hair color and also brighten and restore hair color that has been added to the hair previously. The composition provides conditioning, control, and ease of combing. The color imparted by the leave-in conditioner and dye composition may last in the hair until it is washed out with the next shampoo. A final pH for a leave-in color conditioner of the invention may be, for example, between about 7.5 to about, between about 8.0 to about 8.5, or about 8.5.

Although the applicant does not wish to be bound by any theory, it appears as though the dye molecules are coated by polymers in the formulation and that this provides an easy and efficient color base that can be spread easily throughout the hair. Cationic dyes are compatible in the cationic system and yield a smooth and even coating on the hair shaft. Upon drying, colored film attaches to the hair shaft by having the positive charges on the dye molecules and other polymers attach to the negative charges on the protein molecules of the hair shaft. This creates a stable color that comes off the hair upon shampooing. Color might be removed more gradually in a situation where, for instance, the user is sweating, or after a greatly extended period of time.

EXAMPLES

The following examples further illustrates the present invention and embodiments thereof. All parts and percentages are by weight unless otherwise indicated.

Example 1

Dye Composition with Polectron 430 (International Specialty Products)

A dye composition of the present invention is represented in this example.

|  | Percent Wt. |
|---|---|
| Phase A | |
| Deionized Water | 49.9-51.7 |
| PVP/VA E 365 | 2.0 |
| Tritisol (Croda) | 0.20 |
| Dow Corning Silicone 193 (Dimethicone copolyol for shine) | 0.1 |
| Propylene Glycol | 5.0 |
| Ethyl Alcohol | 20.00 |
| Phase B (choice of one or more dyes) | |
| FD&C Red No. 4 | 0.1-0.3 |
| D&C Red No. 28 | 0.1-3.0 |
| FD&C Red No. 40 | 0.1-3.0 |
| D&C Green No. 5 | 0.1-3.0 |
| FD&C Green No. 3 | 0.1-3.0 |
| D&C Green No. 8 | 0.1-3.0 |
| D&C Yellow No. 10 | 0.1-5.0 |
| D&C Orange No. 4 | 0.1-3.0 |
| Phase C | |
| Polectron ® 430 (International Specialty Products) | 20.00 |

The composition is prepared from the ingredients by adding the deionized water to a stainless steel kettle, then adding the PVP/VA copolymer and mix until clear, because the polymer has completely dissolved. Then add the Tritisol, Silicone 193, propylene glycol, and ethyl alcohol, and stir until clear.

Next add the dyes to the previously prepared mixture, and mix until dyes are completely dissolved and no pieces remain, finally add the Polectron 430 (International Specialty Products) and mix until the color solution is completely uniformly milky. Check, and if needed, adjust shade for final color.

Example 2

Leave-In Conditioner

A leave-in conditioner of the invention is represented in this Example.

| Ingredient | (%) |
|---|---|
| Deionized Water (qs) | Balance to 100% |
| Benzophenone-4 | 0.05 |
| Natrosol (Hercules/Aqualon) | 0.3 |
| Ucare Polymer JR (Amerchol) | 0.7 |
| Hydrolyzed wheat protein | 0.5 |
| Olealkonium Chloride | 0.4 |
| Gafquat 755 (International Specialty Products) | 4.0 |
| Dow Corning 193 | 0.5 |
| Incroquat UV 283 (Croda) | 1.0 |
| Heliogenol (Croda) | 0.2 |
| DMDM Hydantoin | 0.4 |
| Panthenol | 0.05 |
| Glycerin | 8 |
| Lemon Extract | 0.05 |
| Chamomile Extract | 0.05 |
| Rosehips Extract | 0.05 |
| Green Tea Extract | 0.05 |

To make this composition, add the deionized water to kettle, add the benzophenone-4, and mix. Sprinkle in the Natrosol, warm it to 50° C. for 30 minutes while mixing and until the solution is clear. Add Ucare Polymer JR, maintain temperature at 50° C. for another 30 minutes while mixing and until solution is clear. Remove from heat. Add protein, olealkonium chloride, and Gafquat 755, and mix. Add silicone and mix. Add UV 283 and Heliogenol, and mix. Add DMDM Hydantoin and mix. Add Panthenol and mix. Add glycerin, mix. Add remaining ingredients and mix. The resulting pH is between 4.0 and 5.0.

Example 3

Leave-In Color Conditioner

A leave-in color conditioner of the invention is represented in Example 3. To make a leave-in color conditioner of the invention, take a base as described in Example 2, and add a dye composition as described below. In this Example, the ratio of leave-in conditioner to dye composition is 92:8, though in other embodiments of the invention the ratio could be, for example, between 90:10 and 94:6. In general, dark brown colors will require a lower proportion of dye composition.

A formula for a very dark brown shade dye composition is given by way of example. This would be mixed in a 92:8 ratio of leave-in conditioner:dye composition to form a leave-in color conditioner of the invention:

|  | Percent |
|---|---|
| Phase A | |
| Deionized Water | to 100% |
| PVP/VA E 635 | 2.00 |
| Crotein Hydrotriticum QM (Croda) | 0.2 |
| Dimethicone Copolyol Dow Corning 193 | 0.1 |
| Dow Corning 939 | 0.05 |
| Phase B | |
| Deionized Water | 33.0 |
| Arianor Steel Blue (Warner-Jenkinson) | 1.2 |
| Arianor Madder Red (Warner-Jenkinson) | 0.3 |
| Arianor Straw Yellow (Warner-Jenkinson) | 0.6 |
| Arianor Mahogany Brown (Warner-Jenkinson) | 0.2 |
| Arianor Sienna Brown (Warner-Jenkinson) | 0.2 |
| Phase C | |
| Ethyl Alcohol | 20.0 |
| Phase D | |
| Polectron ® 430 (International Specialty Products) | 20.0 |
| Phase E | |
| Triethanolamine 99% | q.s. pH = 8.0-8.5 |
| Phase F | |
| Fragrance | 0.1 |

The dye composition invention can be suitably prepared as follows:

In Phase A, add deionized water to a stainless steel kettle. Then add the PVP/VA copolymer and mix until clear. After the solution is clear and the polymer completely dissolved, add the Crotein Hydrotriticum QM and the dimethicone copolyol and mix until clear. Then add the triethanolamine and check the pH. Adjust to pH 8.0-8.5.

For Phase B (dyes), in a separate stainless steel kettle add deionized water and carefully weigh out the desired cationic dyes for a given shade. Mix until completely dissolved in the solution. Then combine Phases A and B and continue mixing until uniform. Then add Phase C containing the alcohol to the mixed Phases A and B and mix. Then add Phase D and mix. Adjust the pH as indicated. Finally add the perfume component and mix. Check the shade of the final composition.

Mix the leave-in conditioner and the dye composition to form the leave-in color conditioner. Check the shade.

Various modifications may suggest themselves to those skilled in the art with departing from the invention as defined by the following claims.

APPENDIX 1

Sec. 74.101 FD&C Blue No. 1.

(a) Identity. (1) The color additive FD&C Blue No. 1 is principally the disodium salt of ethyl[4-[p-[ethyl(m-sulfobenzyl)amino]-α-(o-sulfophenyl)benzylidene]-2,5-cyclohexadien-1-ylidene](m-sulfobenzyl)ammonium hydroxide inner salt with smaller amounts of the isomeric disodium salts of ethyl[4-[p-[ethyl(p-sulfobenzyl) amino]-α-(o-sulfophenyl)benzylidene]-2,5-cyclohexadien-1-ylidene](p-sulfobenzyl) ammonium hydroxide inner salt and ethyl[4-[p-[ethyl(o-sulfobenzyl)amino]-α-(o-sulfophenyl) benzylidene]-2,5-cyclohexadien-1-ylidene](o-sulfobenzyl) ammonium hydroxide inner salt.

(2) Color additive mixtures for food use (including dietary supplements) made with FD&C Blue No. 1 may contain only those diluents that are suitable and that are listed in part 73 of this chapter as safe for use in color additive mixtures for coloring foods.

(b) Specifications. FD&C Blue No. 1 shall conform to the following specifications and shall be free from impurities other than those named to the extent that such other impurities may be avoided by current good manufacturing practice:

Sum of volatile matter (at 135° C.) and chlorides and sulfates (calculated as sodium salts), not more than 15.0 percent.

Water-insoluble matter, not more than 0.2 percent.

Leuco base, not more than 5 percent.

Sum of o-, m-, and p-sulfobenzaldehydes, not more than 1.5 percent.

N-Ethyl,N-(m-sulfobenzyl)sulfanilic acid, not more than 0.3 percent.

Subsidiary colors, not more than 6.0 percent.

Chromium (as Cr), not more than 50 parts per million.

Manganese (as Mn), not more than 100 parts per million.

Arsenic (as As), not more than 3 parts per million.

Lead (as Pb), not more than 10 parts per million.

Total color, not less than 85.0 percent.

Sec. 74.102 FD&C Blue No. 2.

(a) Identity. (1) The color additive FD&C Blue No. 2 is principally the disodium salt of 2-(1,3-dihydro-3-oxo-5-sulfo-2H-indol-2-ylidene)-2,3-dihydro-3-oxo-1H-indole-5-sulfonic acid (CAS Reg. No. 860-22-0) with smaller amounts of the disodium salt of 2-(1,3-dihydro-3-oxo-7-sulfo-2H-indol-2-ylidene)-2,3-dihydro-3-oxo-1H-indole-5-sulfonic acid (CAS Reg. No. 54947-75-0) and the sodium salt of 2-(1,3-dihydro-3-oxo-2H-indol-2-ylidene)-2,3-dihydro-3-oxo-1H-indole-5-sulfonic acid (CAS Reg. No. 605-18-5). Additionally, FD&C Blue No. 2 is obtained by heating indigo (or indigo paste) in the presence of sulfuric acid. The color additive is isolated and subjected to purification procedures. The indigo (or indigo paste) used above is manufactured by the fusion of N-phenylglycine (prepared from aniline and formaldehyde) in a molten mixture of sodamide and sodium and potassium hydroxides under ammonia pressure. The indigo is isolated and subjected to purification procedures prior to sulfonation.

(2) Color additive mixtures for food use (including dietary supplements) made with FD&C Blue No. 2 may contain only those diluents that are suitable and that are listed in part 73 of this chapter as safe for use in color additive mixtures for coloring foods.

(b) Specifications. The color additive FD&C Blue No. 2 shall conform to the following specifications and shall be free from impurities other than those named to the extent that such other impurities may be avoided by current good manufacturing practice:

Sum of volatile matter at 135° C. (275° F.) and chlorides and sulfates (calculated as sodium salts), not more than 15 percent.

Water insoluble matter, not more than 0.4 percent.

Isatin-5-sulfonic acid, not more than 0.4 percent.

5-Sulfoanthranilic acid, not more than 0.2 percent.

Disodium salt of 2-(1,3-dihydro-3-oxo-7-sulfo-2H-indol-2-ylidene)-2,3-dihydro-3-oxo-1H-indole-5-sulfonic acid, not more than 18 percent.

Sodium salt of 2-(1,3-dihydro-3-oxo-2H-indol-2-ylidene)-2,3-dihydro-3-oxo-1H-indole-5-sulfonic acid, not more than 2 percent.

Lead (as Pb), not more than 10 parts per million.

Arsenic (as As), not more than 3 parts per million.

Mercury (as Hg), not more than 1 part per million.

Total color, not less than 85 percent.

Sec. 74.203 FD&C Green No. 3.

(a) Identity. (1) The color additive FD&C Green No. 3 is principally the inner salt disodium salt of N-ethyl-N-[4-[[4-[ethyl[(3-sulfophenyl)methyl]amino]phenyl](4-hydroxy-2-sulfophenyl)methylene]-2,5-cyclohexadien-1-ylidene]-3-sulfobenzenemethanaminium hydroxide (CAS Reg. No. 2353-45-9); with smaller amounts of the isomeric inner salt disodium salt of N-ethyl-N-[4-[[4-[ethyl[(3-sulfophenyl)methyl]_amino]phenyl](4-hydroxy-2-sulfophenyl)methylene]-2,5-cyclohexadien-1-ylidene]-4-sulfobenzenemethanaminium hydroxide; of N-ethyl-N-[4-[[4-[ethyl[(4-sulfophenyl)methyl]amino]phenyl](4-hydroxy-2-sulfophenyl)methylene]-2,5-cyclohexadien-1-ylidene]-4-sulfobenzenemethanaminium hydroxide and of N-ethyl-N-[4-[[4-[ethyl[(2-sulfophenyl)methyl]amino]phenyl](4-hydroxy-2-sulfophenyl)methylene]-2,5-cyclohexadien-1-ylidene]-3-sulfobenzenemethanaminium hydroxide. Additionally, FD&C Green No. 3 is manufactured by the acid catalyzed condensation of one molecule of 2-formyl-5-hydroxybenzenesulfonic acid with two molecules from a mixture consisting principally of 3-[(ethylphenylamino)methyl]benzensulfonic acid, and smaller amounts of 4-[(ethylphenylamino)methyl]benzenesulfonic acid and 2-[(ethylphenylamino)methyl]benzenesulfonic acid to form the leuco base. The leuco base is then oxidized with lead dioxide and acid or with dichromate and acid to form the dye. The intermediate 2-formyl-5-hydroxybenzenesulfonic acid is prepared by the potassium permanganate oxidation of 2,2'-(1,2-ethenediyl)-bis(5-aminobenzenesulfonic acid) to sodium 5-amino-2-formylbenzenesulfonate. This amine is diazotized and the resulting diazonium salt is hydrolyzed to the desired 2-formyl-5-hydroxybenzenesulfonic acid.

(2) Color additive mixtures for food use (including dietary supplements) made with FD&C Green No. 3 may contain only those diluents that are suitable and that are listed in part 73 of this chapter as safe for use in color additive mixtures for coloring food.

(b) Specifications. The color additive FD&C Green No. 3 shall conform to the following specifications and shall be free from impurities other than those named to the extent that such other impurities may be avoided by current good manufacturing practice:

Sum of volatile matter at 135° C. (275° F.) and chlorides and sulfates (calculated as sodium salts), not more than 15 percent.

Water-insoluble matter, not more than 0.2 percent.

Leuco base, not more than 5 percent.

Sum of 2-, 3-, 4-formylbenzenesulfonic acids, sodium salts, not more than 0.5 percent.

Sum of 3- and 4-[[ethyl(4-sulfophenyl)amino]methyl] benzenesulfonic acid, disodium salts, not more than 0.3 percent.

2-Formyl-5-hydroxybenzenesulfonic acid, sodium salt, not more than 0.5 percent.

Subsidiary colors, not more than 6 percent.

Chromium (as Cr), not more than 50 parts per million.

Arsenic (as As), not more than 3 parts per million.

Lead (as Pb), not more than 10 parts per million.

Mercury (as Hg), not more than 1 part per million.

Total color, not less than 85 percent.

Sec. 74.250 Orange B.

(a) Identity. (1) The color additive Orange B is principally the disodium salt of 1-(4-sulfophenyl)-3-ethylcarboxy-4-(4-sulfonaphthylazo)-5-hydro-xypyrazole.

(2) The diluents in color additive mixtures for food use containing Orange B are limited to those listed in part 73 of this chapter as safe and suitable in color additive mixtures for coloring foods.

(b) Specifications. Orange B shall conform to the following specifications:

Volatile matter (at 135° C.), not more than 6.0 percent.

Chlorides and sulfates (calculated as the sodium salts), not more than 7.0 percent.

Water insoluble matter, not more than 0.2 percent.

1-(4-Sulfophenyl)-3-ethylcarboxy-5-hydroxypyrazolone and 1-(4-sulfophenyl)-3-carboxy-5-hydroxypyrazolone, not more than 0.7 percent.

Naphthionic acid, not more than 0.2 percent.

Phenylhydrazine-p-sulfonic acid, not more than 0.2 percent.

The trisodium salt of 1-(4-sulfophenyl)-3-carboxy-4-(4-sulfonaphthylazo)-5-hydroxypyrazole, not more than 6.0 percent.

Other subsidiary dyes, not more than 1.0 percent.

Lead (as Pb), not more than 10 parts per million.

Arsenic (as As), not more than 1 part per million.

Total color, not less than 87.0 percent.

Sec. 74.302 Citrus Red No. 2.

(a) Identity. (1) The color additive Citrus Red No. 2 is principally 1-(2,5-dimethoxyphenylazo)-2-naphthol.

(2) The following diluents may be used in aqueous suspension, in the percentages specified, to facilitate application to oranges in accordance with paragraph (c)(1) of this section:

(i) Suitable diluents used in accordance with § 73.1 (a) of this chapter.

(ii) Volatile solvents that leave no residue after application to the orange.

(iii) Salts of fatty acids meeting the requirements of § 172.863 of this chapter.

(iv) Sodium tripolyphosphate, not more than 0.05 percent.

(b) Specifications. Citrus Red No. 2 shall conform to the following specifications and shall be free from impurities, other than those named, to the extent that such other impurities may be avoided by good manufacturing practice:

Volatile matter (at 100° C.), not more than 0.5 percent.

Water-soluble matter, not more than 0.3 percent.

Matter insoluble in carbon tetrachloride, not more than 0.5 percent.

Uncombined intermediates, not more than 0.05 percent.

Subsidiary dyes, not more than 2.0 percent.

Lead (as Pb), not more than 10 parts per million.

Arsenic (as As), not more than 1 part per million.

Total color, not less than 98 percent.

Sec. 74.303 FD&C Red No. 3.

(a) Identity. (1) The color additive FD&C Red No. 3 is principally the monohydrate of 9 (o-carboxyphenyl)-6-hydroxy-2,4,5,7-tetraiodo-3H-xanthen-3-one, disodium salt, with smaller amounts of lower imdinated fluoresceins.

(2) Color additive mixtures for food use made with FD&C Red No. 3 may contain only those diluents that are suitable and that are listed in part 73 of this chapter as safe for use in color additive mixtures for coloring foods.

(b) Specifications. FD&C Red No. 3 shall conform to the following specifications and shall be free from impurities other than those named to the extent that such other impurities may be avoided by good manufacturing practice:

Volatile matter (at 135° C.) and chlorides and sulfates (calculated as the sodium salts), total not more than 13 percent.

Water-insoluble matter, not more than 0.2 percent.

Unhalogenated intermediates, total not more than 0.1 percent.

Sodium iodide, not more than 0.4 percent.

Triiodoresorcinol, not more than 0.2 percent.

2(2',4'-Dihydroxy-3',5'-diiodobenzoyl)benzoic acid, not more than 0.2 percent.

Monoiodofluoresceins not more than 1.0 percent.

Other lower iodinated fluoresceins, not more than 9.0 percent.

Lead (as Pb), not more than 10 parts per million.

Arsenic (as As), not more than 3 parts per million.

Total color, not less than 87.0 percent.

Sec. 74.340 FD&C Red No. 40.

(a) Identity. (1) The color additive FD&C Red No. 40 is principally the disodium salt of 6-hydroxy-5-[(2-methoxy-5-methyl-4-sulfophenyl)azo]-2-naphthalenesulfonic acid.

(2) Color additive mixtures for food use (including dietary supplements) made with FD&C Red No. 40 may contain only those diluents that are suitable and that are listed in part 73 of this chapter as safe for use in color additive mixtures for coloring foods.

(3) The listing of this color additive includes lakes prepared as described in § 82.51 of this chapter, except that the color additive used is FD&C Red No. 40 and the resultant lakes meet the specification and labeling requirements prescribed by § 82.51 of this chapter.

(b) Specifications. FD&C Red No. 40 shall conform to the following specifications and shall be free from impurities other than those named to the extent that such other impurities may be avoided by good manufacturing practice:

Sum of volatile matter (at 135° C.) and chlorides and sulfates (calculated as sodium salts), not more than 14.0 percent.

Water-insoluble matter, not more than 0.2 percent.

Higher sulfonated subsidiary colors (as sodium salts), not more than 1.0 percent.

Lower sulfonated subsidiary colors (as sodium salts), not more than 1.0 percent.

Disodium salt of 6-hydroxy-5-[(2-methoxy-5-methyl-4-sulfophenyl)azo]-8-(2-methoxy-5-methyl-4-sulfophenoxy)-2-naphthalenesulfonic acid, not more than 1.0 percent.

Sodium salt of 6-hydroxy-2-naphthalenesulfonic acid (Schaeffer's salt), not more than 0.3 percent.

4-Amino-5-methoxy-o-toluenesulfonic acid, not more than 0.2 percent.

Disodium salt of 6,6'-oxybis(2-naphthalene-sulfonic acid), not more than 1.0 percent.

Lead (as Pb), not more than 10 parts per million.

Arsenic (as As), not more than 3 parts per million.

Total color, not less than 85.0 percent.

Sec. 74.705 FD&C Yellow No. 5.

(a) Identity. (1) The color additive FD&C Yellow No. 5 is principally the trisodium salt of 4,5-dihydro-5-oxo-1-(4-sulfophenyl)-4-[4-sulfophenyl-azo]-1H-pyrazole-3-carboxylic acid (CAS Reg. No. 1934-21-0). To manufacture the additive, 4-amino-benzenesulfonic acid is diazotized using hydrochloric acid and sodium nitrite. The diazo compound is coupled with 4,5-dihydro-5-oxo-1-(4-sulfophenyl)-1H-pyrazole-3-carboxylic acid or with the methyl ester, the ethyl ester, or a salt of this carboxylic acid. The resulting dye is purified and isolated as the sodium salt.

(2) Color additive mixtures for food use made with FD&C Yellow No. 5 may contain only those diluents that are suitable and that are listed in part 73 of this chapter as safe for use in color additive mixtures for coloring foods.

(b) Specifications. FD&C Yellow No. 5 shall conform to the following specifications and shall be free from impurities other than those named to the extent that such other impurities may be avoided by good manufacturing practice:

Sum of volatile matter at 135° C. (275° F.) and chlorides and sulfates (calculated as sodium salts), not more than 13 percent.

Water-insoluble matter, not more than 0.2 percent.

4,4'-[4,5-Dihydro-5-oxo-4-[(4-sulfophenyl)hydrazono]-1H-pyrazol-1,3-diyl]bis[benzenesulfonic acid], trisodium salt, not more than 1 percent.

4-[(4',5-Disulfo[1,1'-biphenyl]-2-yl)hydrazono]-4,5-dihydro-5-oxo-1-(4-sulfophenyl)-1H-pyrazole-3-carboxylic acid, tetrasodium salt, not more than 1 percent.

Ethyl or methyl 4,5-dihydro-5-oxo-1-(4-sulfophenyl)-4-[(4-sulfophenyl)hydrazono]-1H-pyrazole-3-carboxylate, disodium salt, not more than 1 percent.

Sum of 4,5-dihydro-5-oxo-1-phenyl-4-[(4-sulfophenyl)azo]-1H-pyrazole-3-carboxylic acid, disodium salt, and 4,5-dihydro-5-oxo-4-(phenylazo)-1-(4-sulfophenyl)-1H-pyrazole-3-carboxylic acid, disodium salt, not more than 0.5 percent.

4-Aminobenzenesulfonic acid, sodium salt, not more than 0.2 percent.

4,5-Dihydro-5-oxo-1-(4-sulfophenyl)-1H-pyrazole-3-carboxylic acid, disodium salt, not more than 0.2 percent.

Ethyl or methyl 4,5-dihydro-5-oxo-1-(4-sulfophenyl)-1H-pyrazole-3-carboxylate, sodium salt, not more than 0.1 percent.

4,4'-(1-Triazene-1,3-diyl)bis[benzenesulfonic acid], disodium salt, not more than 0.05 percent.

4-Aminoazobenzene, not more than 75 parts per billion.

4-Aminobiphenyl, not more than 5 parts per billion.

Aniline, not more than 100 parts per billion.

Azobenzene, not more than 40 parts per billion.

Benzidine, not more than 1 part per billion.

1,3-Diphenyltriazene, not more than 40 parts per billion.

Lead (as Pb), not more than 10 parts per million.

Arsenic (as As), not more than 3 parts per million.

Mercury (as Hg), not more than 1 part per million.

Total color, not less than 87 percent.

Sec. 74.706 FD&C Yellow No. 6.

(a) Identity. (1) The color additive FD&C Yellow No. 6 is principally the disodium salt of 6-hydroxy-5-[(4-sulfophenyl)azo]-2-naphthalenesulfonic acid (CAS Reg. No. 2783-94-0). The trisodium salt of 3-hydroxy-4-[(4-sulfophenyl)azo]-2,7-naphthalenedisulfonic acid (CAS Reg. No. 50880-65-4) may be added in small amounts. The color additive is manufactured by diazotizing 4-aminobenzenesulfonic acid using hydrochloric acid and sodium nitrite or sulfuric acid and sodium nitrite. The diazo compound is coupled with 6-hydroxy-2-naphthalene-sulfonic acid. The dye is isolated as the sodium salt and dried. The trisodium salt of 3-hydroxy-4-[(4-sulfophenyl)azo]-2,7-naphthalenedisulfonic acid which may be blended with the principal color is prepared in the same manner except the diazo benzenesulfonic acid is coupled with 3-hydroxy-2,7-naphthalenedisulfonic acid.

(2) Color additive mixtures for food use made with FD&C Yellow No. 6 may contain only those diluents that are suitable and that are listed in part 73 of this chapter as safe for use in color additive mixtures for coloring foods.

(b) Specifications. The color additive FD&C Yellow No. 6 shall conform to the following specifications and shall be free from impurities other than those named to the extent that such other impurities may be avoided by current good manufacturing practice:

Sum of volatile matter (at 135° C.) and chlorides and sulfates (calculated as sodium salts), not more than 13 percent.

Water insoluble matter, not more than 0.2 percent.

Sodium salt of 4-aminobenzenesulfonic acid, not more than 0.2 percent.

Sodium salt of 6-hydroxy-2-naphthalenesulfonic acid, not more than 0.3 percent.

Disodium salt of 6,6'-oxybis[2-naphthalenesulfonic acid], not more than 1 percent.

Disodium salt of 4,4'-(1-triazene-1,3-diyl)bis[benzenesulfonic acid], not more than 0.1 percent.

Sum of the sodium salt of 6-hydroxy-5-(phenylazo)-2-naphthalenesulfonic acid and the sodium salt of 4-[(2-hydroxy-1-naphthalenyl)azo]benzenesulfonic acid, not more than 1 percent.

Sum of the trisodium salt of 3-hydroxy-4-[(4-sulfophenyl)azo]-2,7-naphthalenedisulfonic acid and other higher sulfonated subsidiaries, not more than 5 percent.

4-Aminoazobenzene, not more than 50 parts per billion.

4-Aminobiphenyl, not more than 15 parts per billion.

Aniline, not more than 250 parts per billion.

Azobenzene, not more than 200 parts per billion.

Benzidine, not more than 1 part per billion.

1,3-Diphenyltriazene, not more than 40 parts per billion.

1-(Phenylazo)-2-naphthalenol, not more than 10 parts per million.

Lead (as Pb), not more than 10 parts per million.

Arsenic (as As), not more than 3 parts per million.

Mercury (as Hg), not more than 1 part per million.

Total color, not less than 87 percent.

Sec. 74.1101 FD&C Blue No. 1

(a) Identity. (1) For ingested drugs, the color additive FD&C Blue No. 1 shall conform in identity to the requirements of § 74.101(a)(1).

(2) For externally applied drugs, the color additive FD&C Blue No. 1 shall conform in identity to the requirements of § 74.2101(a).

(3) Color additive mixtures for drug use made with FD&C Blue No. 1 may contain only those diluents that are suitable and that are listed in part 73 of this chapter as safe for use in color additive mixtures for coloring drugs.

(b) Specifications. (1) The color additive FD&C Blue No. 1 for use in coloring drugs generally shall conform in specifications to the requirements of § 74.101(b).

(2) FD&C Blue No. 1 Aluminum Lake shall be prepared in accordance with the requirements of § 82.51 of this chapter.

(c) Uses and restrictions. (1) FD&C Blue No. 1 may be safely used for coloring drugs, including drugs intended for use in the area of the eye, in amounts consistent with current good manufacturing practice.

(2) FD&C Blue No. 1 Aluminum Lake may be safely used for coloring drugs intended for use in the area of the eye, in amounts consistent with current good manufacturing practice, subject to the restrictions on the use of color additives in § 70.5(b) and (c) of this chapter.

Sec. 74.1102 FD&C Blue No. 2.

(a) Identity. (1) The color additive FD&C Blue No. 2 shall conform in identity to the requirements of § 74.102(a)(1).

(2) Color additive mixtures for use in ingested drugs made with FD&C Blue No. 2 may contain only those diluents that are suitable and that are listed in part 73 of this chapter as safe for use in color additive mixtures for coloring drugs.

(b) The color additive FD&C Blue No. 2 for use in coloring ingested drugs shall conform to the specifications in § 74.102(b).

Sec. 74.1104 D&C Blue No. 4.

(a) Identity. (1) The color additive D&C Blue No. 4 is principally the diammonium salt of ethyl[4-[p[ethyl(m-sulfobenzyl)ami-no]-α-(o-sulfophenyl)benzylidene]-2,5-cyclo-hexadien-1-ylidene](m-sulfobenzyl)ammonium hydroxide inner salt with smaller amounts of the isomeric diammonium salts of ethyl[4-[p-[ethyl(p-sulfobenzyl)amino]-α-(o-sulfophenyl)benzylidene]-2,5-cyclohexadien-1-ylidene](p-sulfobenzyl) ammonium hydroxide inner salt and ethyl[4-[p-[ethyl(o-sulfobenzyl)amino]-α-(o-sulfophenyl)benzylidene]-2,5-cyclohexadien-1-ylidene](o-sulfobenzyl)ammonium hydroxide inner salt.

(2) Color additive mixtures for use in externally applied drugs made with D&C Blue No. 4 may contain only those diluents that are suitable and that are listed in part 73 of this chapter for use in color additive mixtures for coloring externally applied drugs.

(b) Specifications. D&C Blue No. 4 shall conform to the following specifications and shall be free from impurities other than those named to the extent that such impurities may be avoided by good manufacturing practice:

Sum of volatile matter (at 135° C.) and chlorides and sulfates (calculated as sodium salts), not more than 15 percent.

Water-insoluble matter, not more than 0.2 percent.

Leuco base, not more than 5 percent.

Sum of o-, m, and p-sulfobenzaldehydes, ammonium salt, not more than 1.5 percent.

N-ethyl, N-(m-sulfobenzyl)sulfanilic acid ammonium salt, not more than 0.3 percent.

Subsidiary colors, not more than 6 percent.

Chromium (as Cr), not more than 50 parts per million.

Lead (as Pb), not more than 20 parts per million.

Arsenic (as As), not more than 3 parts per million.

Mercury (as Hg), not more than 1 part per million.

Total color, not less than 85 percent.

Sec. 74.1109 D&C Blue No. 9.

(a) Identity. The color additive D&C Blue No. 9 is principally 7,16-dichloro-6,15-dihydro-5,9,14,18-anthrazine-tetrone.

(b) Specifications. D&C Blue No. 9 shall conform to the following specifications and shall be free from impurities other than those named to the extent that such impurities may be avoided by good manufacturing practice:

Volatile matter (at 135° C.), not more than 3 percent.

Matter extractable by alcoholic HCl (0.1 ml of concentrated hydrochloric acid per 50 ml of 95 percent ethyl alcohol), not more than 1 percent.

2-Amino anthraquinone, not more than 0.2 percent.

Organically combined chlorine in pure dye, 13.0-14.8 percent.

Lead (as Pb), not more than 20 p/m.

Arsenic (as As), not more than 3 p/m.

Total color, not less than 97 percent.

Sec. 74.1203 FD&C Green No. 3.

(a) Identity and specifications. (1) The color additive FD&C Green No. 3 shall conform in identity and specifications to the requirements of § 74.203(a)(1) and (b).

(2) Color additive mixtures for drug use made with FD&C Green No. 3 may contain only those diluents that are suitable and that are listed in part 73 of this chapter as safe for use in color additive mixtures for coloring drugs.

(b) Uses and restrictions. The color additive FD&C Green No. 3 may be safely used for coloring drugs generally in amounts consistent with current good manufacturing practice.

Sec. 74.1205 D&C Green No. 5.

(a) Identity. (1) The color additive D&C Green No. 5 is principally the disodium salt of 2,2'-[(9,10-dihydro-9,10-dioxo-1,4-anthracenediyl)diimino]bis-[5-methylbenzenesulfonic acid](CAS Reg. No. 4403-90-1).

(2) Color additive mixtures for use in drugs made with D&C Green No. 5 may contain only those diluents that are suitable and those that are listed in part 73 of this chapter for use in color additive mixtures for coloring drugs.

(b) Specifications. (1) D&C Green No. 5 for use in coloring surgical sutures shall conform to the following specifications and shall be free from impurities other than those named to the extent that such impurities may be avoided by current good manufacturing practice:

Sum of volatile matter (at 135° C.) and chlorides and sulfates (calculated as sodium salts), not more than 20 percent.

Water insoluble matter, not more than 0.2 percent.

1,4-Dihydroxyanthraquinone, not more than 0.2 percent.

2-Amino-m-toluenesulfonic acid, not more than 0.2 percent.

Subsidiary colors, not more than 5 percent.

Lead (as Pb), not more than 10 parts per million.

Arsenic (as As), not more than 3 parts per million.

Total color, not less than 80 percent.

(2) D&C Green No. 5 for use in coloring drugs shall conform to the following specifications and shall be free from impurities other than those named to the extent that such other impurities may be avoided by current good manufacturing practice:

Sum of volatile matter (at 135° C.) and chlorides and sulfates (calculated as sodium salts), not more than 20 percent.

Water-insoluble matter, not more than 0.2 percent.

1,4-Dihydroxyanthraquinone, not more than 0.2 percent.

Sulfonated toluidines, total not more than 0.2 percent.

p-Toluidine, not more than 0.0015 percent.

Sum of monosulfonated D&C Green No. 6 and Ext. D&C Violet No. 2, not more than 3 percent.

Lead (as Pb), not more than 20 parts per million.

Arsenic (as As), not more than 3 parts per million.

Mercury (as Hg), not more than 1 part per million.

Total color, not less than 80 percent.

Sec. 74.1206 D&C Green No. 6.

(a) Identity. The color additive D&C Green No. 6 is 1,4-bis[(4-methylphenyl)amino]-9,10-anthracenedione (CAS. Reg. No. 128-80-3).

(b) Specifications. The color additive D&C Green No. 6 for use in coloring externally applied drugs shall conform to the following specifications and shall be free from impurities other than those named to the extent that such other impurities may be avoided by current good manufacturing practice:

Volatile matter (at 135° C.), not more than 2.0 percent.

Water-soluble matter, not more than 0.3 percent.

Matter insoluble in carbon tetrachloride, not more than 1.5 percent.

p-Toluidine, not more than 0.1 percent.

1,4-Dihydroxyanthraquinone, not more than 0.2 percent.

1-Hydroxy-4-[(4-methylphenyl)amino]-9,10-anthracenedione, not more than 5.0 percent.

Lead (as Pb), not more than 20 parts per million.

Arsenic (as As), not more than 3 parts per million.

Mercury (as Hg), not more than 1 part per million.

Total color, not less than 96.0 percent.

Sec. 74.1208 D&C Green No. 8.

(a) Identity. (1) The color additive D&C Green No. 8 is principally the trisodium salt of 8-hydroxy-1,3,6-pyrenetrisulfonic acid.

(2) Color additive mixtures for use in externally applied drugs made with D&C Green No. 8 may contain only those diluents that are suitable and that are listed in part 73 of this chapter for use in color additive mixtures for coloring externally applied drugs.

(b) Specifications. D&C Green No. 8 shall conform to the following specifications and shall be free from impurities other than those named to the extent that such impurities may be avoided by good manufacturing practices:

Volatile matter (at 135° C.), not more than 15 percent.

Water-insoluble matter, not more than 0.2 percent.

Chlorides and sulfates (calculated as sodium salt), not more than 20 percent.

The trisodium salt of 1,3,6-pyrenetrisulfonic acid, not more than 6 percent.

The tetrasodium salt of 1,3,6,8-pyrenetetrasulfonic acid, not more than 1 percent.

Pyrene, not more than 0.2 percent.

Lead (as Pb), not more than 20 parts per million.

Arsenic (as As), not more than 3 parts per million.

Mercury (as Hg), not more than 1 part per million.

Total color, not less than 65 percent.

Sec. 74.1254 D&C Orange No. 4.

(a) Identity. (1) the color additive D&C Orange No. 4 is principally the sodium salt of 4-[(2-hydroxy-1-naphthalenyl)azo]benzenesulfonic acid.

(2) Color additive mixtures for use in externally applied drugs made with D&C Orange No. 4 may contain only those diluents that are suitable and that are listed in part 73 of this chapter for use in color additive mixtures for coloring externally applied drugs.

(b) Specifications. D&C Orange No. 4 shall conform to the following specifications and shall be free from impurities other than those named to the extent that such impurities may be avoided by good manufacturing practice.

Sum of volatile matter (at 135° C.) and chlorides and sulfates (calculated as sodium salts), not more than 13 percent.

Water-insoluble matter, not more than 0.2 percent.

2-Naphthol, not more than 0.4 percent.

Sulfanilic acid, sodium salt, not more than 0.2 percent.

Subsidiary colors, not more than 3 percent.

4,4'-(Diazoamino)-dibenzenesulfonic acid, not more than 0.1 percent.

Lead (as Pb), not more than 20 parts per million.

Arsenic (as As), not more than 3 parts per million.

Mercury (as Hg), not more than 1 part per million.

Total color, not less than 87 percent.

Sec. 74.1255 D&C Orange No. 5.

(a) Identity. (1) the color additive D&C Orange No. 5 is a mixture consisting principally the sodium salt of 4',5'-dibromofluorescein (CAS Reg. No. 596-03-2) and 2',4',5'-tribromofluorescein (CAS Reg. No. 25709-83-5) and 2',4',5',7'-tetrabromofluorescein (CAS Reg. No. 15086-94-9). D&C Orange No. 5 is manufactured by brominating fluorescein with elemental bromine. The fluorescein is manufactured by the acid condensation of resorcinol and phthalic acid or its anhydride. The fluorescein is isolated and partially purified prior to bromination.

(2) Color additive mixtures for drug use made with D&C Orange No. 5 may contain only those diluents that are suitable and that are listed in part 73 of this chapter for use in color additive mixtures for coloring drugs.

(b) Specifications. D&C Orange No. 5 shall conform to the following specifications and shall be free from impurities other than those named to the extent that such impurities may be avoided by good manufacturing practice.

4',5'-dibromofluorescein, not less than 50 percent and not more than 65 percent.

2',4',5'-tribromofluorescein, not less than 30 percent and not more than 40 percent.

2',4',5',7'-tetrabromofluorescein, not more than 10 percent.

Sum of 2',4'-dibromofluorescein and 2',5'-dibromofluorescein, not more than 2 percent.

4'-Bromofluorescein, not more than 2 percent.
Fluorescein, not more than 1 percent.
Phthalic acid, not more than 1 percent.
2-(3,5-Dibromo-2,4-dihydroxybenzoyl)benzoic acid, not more than 0.5 percent.
Brominated resorcinol, not more than 0.4 percent.
Sum of volatile matter (at 135° C.) and halides and sulfates (calculated as sodium salts), not more than 10 percent.
Insoluble matter (alkaline solution), not more than 0.3 percent.
Lead (as Pb), not more than 20 parts per million.
Arsenic (as As), not more than 3 parts per million.
Mercury (as Hg), not more than 1 part per million.
Total color, not less than 90 percent.

Sec. 74.1260 D&C Orange No. 10.

(a) Identity. (1) The color additive D&C Orange No. 10 is a mixture consisting principally of 4',5'-diiodofluorescein, 2',4',5'-triiodofluorescein, and 2',4',5',7'-tetraiodofluorescein.

(2) Color additive mixtures for drug use made with D&C Orange No. 10 may contain only those diluents listed in this subpart as safe and suitable for use in color additive mixtures for coloring externally applied drugs.

(b) Specifications. D&C Orange No. 10 shall conform to the following specifications and shall be free from impurities other than those named to the extent that such other impurities may be avoided by good manufacturing practice:

Sum of volatile matter (at 135° C.) and halides and sulfates (calculated as sodium salts), not more than 8 percent.
Insoluble matter (alkaline solution), not more than 0.5 percent.
Phthalic acid, not more than 0.5 percent.
2-[3',5'-Diiodo-2',4'-dihydroxybenzoyl]benzoic acid, not more than 0.5 percent.
Fluorescein, not more than 1 percent.
4'-Iodofluorescein, not more than 3 percent.
2',4'-Diiodofluorescein and 2',5'-diiodofluorescein, not more than 2 percent.
2',4',5'-Triiodofluorescein, not more than 35 percent.
2',4',5',7'-Tetraiodofluorescein, not more than 10 percent.
4',5'-Diiodofluorescein, not less than 60 percent and not more than 95 percent.
Lead (as Pb), not more than 20 parts per million.
Arsenic (as As), not more than 3 parts per million.
Mercury (as Hg), not more than 1 part per million.
Total color, not less than 92 percent.

Sec. 74.1261 D&C Orange No. 11.

(a) Identity. (1) The color additive D&C Orange No. 11 is a mixture consisting principally of the disodium salts of 4',5'-diiodofluorescein, 2',4',5'-triiodofluorescein and 2',4',5',7'-tetraiodofluorescein.

(2) Color additive mixtures for drug use made with D&C Orange No. 11 may contain only those diluents listed in this subpart as safe and suitable for use in color additive mixtures for coloring externally applied drugs.

(b) Specifications. The color additive D&C Orange No. 11 shall conform to the following specifications and shall be free from impurities other than those named to the extent that such impurities may be avoided by good manufacturing practice:

Sum of volatile matter (at 135° C.) and halides and sulfates (calculated as sodium salts), not more than 8 percent.
Water-insoluble matter, not more than 0.5 percent.
Phthalic acid, not more than 0.5 percent.
2-[3',5'-Diiodo-2',4'-dihydroxybenzoyl]benzoic acid, sodium salt, not more than 0.5 percent.
Fluorescein, disodium salt, not more than 1 percent.
4'-Iodofluorescein, disodium salt, not more than 3 percent.
2',4'-Diiodofluorescein and 2',5'-diiodofluorescein, not more than 2 percent.
2',4',5'-Triiodofluorescein, not more than 35 percent.
2',4',5',7'-Tetraiodofluorescein, disodium salt, not more than 10 percent.
4',5'-Diiodofluorescein, disodium salt, not less than 60 percent and not more than 95 percent.
Lead (as Pb), not more than 20 parts per million.
Arsenic (as As), not more than 3 parts per million.
Mercury (as Hg), not more than 1 part per million.
Total color, not less than 92 percent.

Sec. 74.1303 FD&C Red No. 3.

(a) Identity and specifications. (1) The color additive FD&C Red No. 3 shall conform in identity and specifications to the requirements of § 74.303(a)(1) and (b).

(2) Color additive mixtures for ingested drug used made with FD&C Red No. 3 may contain only those diluents that are suitable and that are listed in part 73 of this chapter as safe for use in color additive mixtures for coloring ingested drugs.

(b) Uses and restrictions. FD&C Red No. 3 may be safely used for coloring ingested drugs in amounts consistent with good manufacturing practice.

Sec. 74.1304 FD&C Red No. 4.

(a) Identity. (1) The color additive FD&C Red No. 4 is principally the disodium salt of 3-[(2,4-dimethyl-5-sulfophenyl)azo]-4-hydroxy-1-naphthalenesulfonic acid.

(2) Color additive mixtures for use in externally applied drugs made with FD&C Red No. 4 may contain only those diluents that are suitable and that are listed in part 73 of this chapter for use in color additive mixtures for coloring externally applied drugs.

(b) Specifications. FD&C Red No. 4 shall conform to the following specifications and shall be free from impurities other than those named to the extent that such impurities may be avoided by good manufacturing practice:

Sum of volatile matter (at 135° C.) and chlorides and sulfates (calculated as sodium salts), not more than 13 percent.
Water-insoluble matter, not more than 0.2 percent.
5-Amino-2,4-dimethyl-1-benzenesulfonic acid, sodium salt, not more than 0.2 percent.
4-Hydroxy-1-naphthalenesulfonic acid, sodium salt, not more than 0.2 percent.
Subsidiary colors, not more than 2 percent.
Lead (as Pb), not more than 10 parts per million.
Arsenic (as As), not more than 3 parts per million.
Mercury (as Hg), not more than 1 part per million.

Total color, not less than 87 percent.

Sec. 74.1306 D&C Red No. 6.

(a) Identity. (1) The color additive D&C Red No. 6 is principally the disodium salt of 3-hydroxy-4-[(4-methyl-2-sulfophenyl)azo]-2-naphthalenecarboxylic acid (CAS Reg. No. 5858-81-1). To manufacture the additive, 2-amino-5-methylbenzenesulfonic acid is diazotized with hydrochloric acid and sodium nitrite. The diazo compound is coupled in alkaline medium with 3-hydroxy-2-naphthalenecarboxylic acid. The resulting dye precipitates as the disodium salt.

(2) Color additive mixtures for drug use made with D&C Red No. 6 may contain only those diluents that are suitable and that are listed in part 73 of this chapter as safe for use in color additive mixtures for coloring drugs.

(b) Specifications. The color additive D&C Red No. 6 shall conform to the following specifications and shall be free from impurities other than those named to the extent that such impurities may be avoided by current good manufacturing practice:

Sum of volatile matter (at 135° C.) and chlorides and sulfates (calculated as sodium salts), not more than 10 percent.

Ether-soluble matter, passes test entitled "The Procedure for Determining Ether-Soluble Material in D&C Red Nos. 6 and 7," which is an Appendix A to part 74.

2-Amino-5-methylbenzenesulfonic acid, sodium salt, not more than 0.2 percent.

3-Hydroxy-2-naphthalenecarboxylic acid, sodium salt, not more than 0.4 percent.

3-Hydroxy-4-[(4-methylphenyl)azo]-2-naphthalenecarboxylic acid, sodium salt, not more than 0.5 percent.

p-Toluidine, not more than 15 parts per million.

Lead (as Pb), not more than 20 parts per million.

Arsenic (as As), not more than 3 parts per million.

Mercury (as Hg), not more than 1 part per million.

Total color, not less than 90 percent.

Sec. 74.1307 D&C Red No. 7.

(a) Identity. (1) The color additive D&C Red No. 7 is principally the calcium salt of 3-hydroxy-4-[(4-methyl-2-sulfophenyl)azo]-2-naphthalenecarboxylic acid (CAS Reg. No. 5281-04-9). To manufacture the additive, 2-amino-5-methylbenzenesulfonic acid is diazotized with hydrochloric acid and sodium nitrite. The diazo compound is coupled in alkaline medium with 3-hydroxy-2-naphthalenecarboxylic acid and the resulting dye converted to the calcium salt with calcium chloride.

(2) Color additive mixtures for drug use made with D&C Red No. 7 may contain only those diluents that are suitable and that are listed in part 73 of this chapter as safe for use in color additive mixtures for coloring drugs.

(b) Specifications. The color additive D&C Red No. 7 shall conform to the following specifications and shall be free from impurities other than those named to the extent that such impurities may be avoided by current good manufacturing practice:

Sum of volatile matter (at 135° C.) and chlorides and sulfates (calculated as sodium salts), not more than 10 percent.

Ether-soluble matter, passes test entitled "The Procedure for Determining Ether-soluble Material in D&C Red Nos. 6 and 7," which is an Appendix A to part 74.

2-Amino-5-methylbenzenesulfonic acid, calcium salt, not more than 0.2 percent.

3-Hydroxy-2-naphthalenecarboxylic acid, calcium salt, not more than 0.4 percent.

3-Hydroxy-4-[(4-methylphenyl)azo]-2-naphthalenecarboxylic acid, calcium salt, not more than 0.5 percent.

p-Toluidine, not more than 15 parts per million.

Lead (as Pb), not more than 20 parts per million.

Arsenic (as As), not more than 3 parts per million.

Mercury (as Hg), not more than 1 part per million.

Total color, not less than 90 percent.

Sec. 74.1317 D&C Red No. 17.

(a) Identity. (1) The color additive D&C Red No. 17 is principally 1-[[4-(phenylazo)phenyl]azo]-2-naphthalenol.

(2) Color additive mixtures for drug use made with D&C Red No. 17 may contain only those diluents that are suitable and that are listed in part 73 of this chapter as safe for use in color additive mixtures for coloring externally applied drugs.

(b) Specifications. D&C Red No. 17 shall conform to the following specifications and shall be free from impurities, other than those named, to the extent that such other impurities may be avoided by good manufacturing practice:

Volatile matter (at 135° C.), not more than 5 percent.

Matter insoluble in both toluene and water (color additive mixed in toluene and the resultant residue isolated and mixed with water to obtain the matter insoluble in both toluene and water), not more than 0.5 percent.

Chlorides and sulfates (calculated as sodium salts), not more than 3 percent.

Aniline, not more than 0.2 percent.

4-Aminoazobenzene, not more than 0.1 percent.

2-Naphthol, not more than 0.2 percent.

1-(Phenylazo)-2-naphthol, not more than 3 percent.

1-[[2-(phenylazo)phenyl]azo]-2-naphthalenol, not more than 2 percent.

Lead (as Pb), not more than 20 parts per million.

Arsenic (as As), not more than 3 parts per million.

Mercury (as Hg), not more than 1 part per million.

Total color, not less than 90 percent.

Sec. 74.1321 D&C Red No. 21.

(a) Identity. (1) The color additive D&C Red No. 21 is principally 2',4',5',7'-tetrabromofluorescein (CAS Reg. No. 15086-94-9), and may contain smaller amounts of 2',4',5'-tribromofluorescein (CAS Reg. No. 25709-83-5) and 2',4',7' ȏtribromofluorescein (CAS Reg. No. 25709-84-6). The color additive is manufactured by brominating fluorescein with elemental bromine. The fluorescein is manufactured by the acid condensation of resorcinol and phthalic acid or its anhydride. The fluorescein is isolated and partially purified prior to bromination.

(2) Color additive mixtures for drug use made with D&C Red No. 21 may contain only those diluents that are suitable and that are listed in part 73 of this chapter as safe for use in color additive mixtures for coloring drugs.

(b) Specifications. The color additive D&C Red No. 21 shall conform to the following specifications and shall be free from impurities other than those named to the extent that such impurities may be avoided by current good manufacturing practice:

Sum of volatile matter (at 135° C.) and halides and sulfates (calculated as sodium salts), not more than 10 percent.

Insoluble matter (alkaline solution), not more than 0.5 percent.

Phthalic acid, not more than 1 percent.

2-(3,5-Dibromo-2,4-dihydroxybenzoyl)benzoic acid, not more than 0.5 percent.

2',4',5',7'-Tetrabromofluorescein, ethyl ester, not more than 1 percent.

Brominated resorcinol, not more than 0.4 percent.

Fluorescein, not more than 0.2 percent.

Sum of mono- and dibromofluoresceins, not more than 2 percent.

Tribromofluoresceins, not more than 11 percent.

2',4',5',7'-Tetrabromofluorescein, not less than 87 percent.

Lead (as Pb), not more than 20 parts per million.

Arsenic (as As), not more than 3 parts per million.

Mercury (as Hg), not more than 1 part per million.

Total color, not less than 90 percent.

Sec. 74.1322 D&C Red No. 22.

(a) Identity. (1) The color additive D&C Red No. 22 is principally the disodium salt of 2',4',5'7'-tetrabromofluorescein (CAS Reg. No. 17372-87-1) and may contain smaller amounts of the disodium salts of 2',4',5'-tribromofluorescein and 2',4',7'-tribromofluorescein. The color additive is manufactured by alkaline hydrolysis of 2',4',5',7'-tetrabromofluorescein. 2',4',5',7'-Tetrabromofluorescein is manufactured by brominating fluorescein with elemental bromine. The fluorescein is manufactured by the acid condensation of resorcinol and phthalic acid or its anhydride. Fluorescein is isolated and partially purified prior to bromination.

(2) Color additive mixtures for drug use made with Red No. 22 may contain only those diluents that are suitable and that are listed in part 73 of this chapter as safe for use in color additive mixtures for coloring drugs.

(b) Specifications. The color additive D&C Red No. 22 shall conform to the following specifications and shall be free from impurities other than those named to the extent that such impurities may be avoided by current good manufacturing practice:

Sum of volatile matter (at 135° C.) and halides and sulfates (calculated as soduim salts), not more than 10 percent.

Water-insoluble matter not more than 0.5 percent.

Disodium salt of phthalic acid, not more than 1 percent.

Sodium salt of 2-(3,5-Dibromo-2,4-dihydroxybenzoyl) benzoic acid, not more than 0.5 percent.

2',4',5',7'-Tetrabromofluorescein, ethyl ester, not more than 1 percent.

Brominated resorcinol, not more than 0.4 percent.

Sum of disodium salts of mono- and dibromofluoresceins, not more than 2 percent.

Sum of disodium salts of tribromofluoresceins, not more than 25 percent.

Disodium salt of 2',4',5',7'-Tetrabromofluorescein, not less than 72 percent.

Lead (as Pb), not more than 20 parts per million.

Arsenic (as As), not more than 3 parts per million.

Mercury (as Hg), not more than 1 part per million.

Total color, not less than 90 percent.

Sec. 74.1327 D&C Red No. 27.

(a) Identity. (1) The color additive D&C Red No. 27 is principally 2',4',5',7'-tetrabromo-4,5,6,7-tetrachlorofluorescein (CAS Reg. No. 13473-26-2). The color additive is manufactured by brominating 4,5,6,7-tetrachlorofluorescein with elemental bromine. The 4,5,6,7-tetrachlorofluorescein is manufactured by the acid condensation of resorcinol and tetrachlorophthalic acid or its anhydride. The 4,5,6,7-tetrachlorofluorescein is isolated and partially purified prior to bromination.

(2) Color additive mixtures for drug use made with D&C Red No. 27 may contain only those diluents that are suitable and that are listed in part 73 of this chapter as safe for use in color additive mixtures for coloring drugs.

(b) Specifications. D&C Red No. 27 shall conform to the following specifications and shall be free from impurities other than those named to the extent that such impurities may be avoided by current good manufacturing practice:

Sum of volatile matter (at 135° C.) and halides and sulfates (calculated as sodium salts), not more than 10 percent.

Insoluble matter (alkaline solution), not more than 0.5 percent.

Tetrachlorophthalic acid, not more than 1.2 percent.

Brominated resorcinol, not more than 0.4 percent.

2,3,4,5-Tetrachloro-6-(3,5-dibromo-2,4-dihydroxybenzoyl)benzoic acid, not more than 0.7 percent.

2',4',5',7'-Tetrabromo-4,5,6,7-tetrachlorofluorescein, ethyl ester, not more than 2 percent.

Lower halogenated subsidiary colors, not more than 4 percent.

Lead (as Pb), not more than 20 parts per million.

Arsenic (as As), not more than 3 parts per million.

Mercury (as Hg), not more than 1 part per million.

Total color, not less than 90 percent.

Sec. 74.1328 D&C Red No. 28.

(a) Identity. (1) The color additive D&C Red No. 28 is principally the disodium salt of 2',4',5',7'-tetrabromo-4,5,6,7-tetrachlorofluorescein (CAS Reg. No. 18472-87-2) formed by alkaline hydrolysis of the parent tetrabromotetrachlorofluorescein.

(2) Color additive mixtures for drug use made with D&C Red No. 28 may contain only those diluents that are suitable and that are listed in part 73 of this chapter as safe for use in color additive mixtures for coloring drugs.

(b) Specifications. D&C Red No. 28 shall conform to the following specifications and shall be free from impurities other than those named to the extent that such impurities may be avoided by current good manufacturing practice:

Sum of volatile matter (at 135° C.) and halides and sulfates (calculated as sodium salts), not more than 15 percent.

Insoluble matter (alkaline solution), not more than 0.5 percent.

Tetrachlorophthalic acid, not more than 1.2 percent.

Brominated resorcinol, not more than 0.4 percent.

2,3,4,5-Tetrachloro-6-(3,5-dibromo-2,4-dihydroxybenzoyl)benzoic acid, not more than 0.7 percent.

2',4',5',7'-Tetrabromo-4,5,6,7-tetrachlorofluorescein, ethyl ester, not more than 2 percent.

Lower halogenated subsidiary colors, not more than 4 percent.

Lead (as Pb), not more than 20 parts per million.

Arsenic (as As), not more than 3 parts per million.

Mercury (as Hg), not more than 1 part per million.

Total color, not less than 85 percent.

Sec. 74.1330 D&C Red No. 30.

(a) Identity. (1) The color additive D&C Red No. 30 is principally 6-chloro-2-(6-chloro-4-methyl-3-oxobenzo[b]thien-2(3H)-ylidene)-4-methyl-benzo[b]thiophen-3(2H)-one (CAS Reg. No. 2379-74-0).

(2) Color additive mixtures for drug use made with D&C Red No. 30 may contain only those diluents that are suitable and that are listed in part 73 of this chapter as safe for use in color additive mixtures for coloring drugs.

(b) Specifications. D&C Red No. 30 shall conform to the following specifications and shall be free from impurities other than those named to the extent that such impurities may be avoided by current good manufacturing practice:

Volatile matter (at 135° C.), not more than 5 percent.

Chlorides and sulfates (calculated as sodium salts), not more than 3 percent.

Matter soluble in acetone, not more than 5 percent.

Total color, not less than 90 percent.

Lead (as Pb), not more than 20 parts per million.

Arsenic (as As), not more than 3 parts per million.
Mercury (as Hg), not more than 1 part per million.

Sec. 74.1331 D&C Red No. 31.

(a) Identity. (1) The color additive D&C Red No. 31 is principally the calcium salt of 3-hydroxy-4-(phenylazo)-2-naphthalenecarboxylic acid.

(2) Color additive mixtures for drug use made with D&C Red No. 31 may contain only those diluents that are suitable and that are listed in part 73 of this chapter as safe for use in color additive mixtures for coloring externally applied drugs.

(b) Specifications. D&C Red No. 31 shall conform to the following specifications and shall be free from impurities, other than those named, to the extent that such other impurities may be avoided by good manufacturing practice:

Sum of volatile matter (at 135° C.) and chlorides and sulfates (calculated as sodium salts), not more than 10 percent.

Aniline, not more than 0.2 percent.
3-Hydroxy-2-naphthoic acid, calcium salt, not more than 0.4 percent.
Subsidiary colors, not more than 1 percent.
Lead (as Pb), not more than 20 parts per million.
Arsenic (as As), not more than 3 parts per million.
Mercury (as Hg), not more than 1 part per million.
Total color, not less than 90 percent.

Sec. 74.1333 D&C Red No. 33.

(a) Identity. (1) The color additive D&C Red No. 33 is principally the disodium salt of 5-amino-4-hydroxy-3-(phenylazo)-2,7-naphthalenedisulfonic acid (CAS Reg. No. 3567-66-6). To manufacture the additive, the product obtained from the nitrous acid diazotization of aniline is coupled with 4-hydroxy-5-amino-2,7-naphthalenedisulfonic acid in an alkaline aqueous medium. The color additive is isolated as the sodium salt.

(2) Color additive mixtures for drug use made with D&C Red No. 33 may contain only those diluents that are suitable and that are listed in part 73 of this chapter as safe for use in color additive mixtures for coloring drugs.

(b) Specifications. D&C Red No. 33 shall conform to the following specifications and shall be free from impurities other than those named to the extent that such impurities may be avoided by current good manufacturing practices:

Sum of volatile matter at 135° C. (275° F.) and chlorides and sulfates (calculated as sodium salts), not more than 18 percent.

Water-insoluble matter, not more than 0.3 percent.
4-Amino-5-hydroxy-2,7-naphthalenedisulfonic acid, disodium salt, not more than 0.3 percent.
4,5-Dihydroxy-3-(phenylazo)-2,7-naphthalenedisulfonic acid, disodium salt, not more than 3.0 percent.
Aniline, not more than 25 parts per million.
4-Aminoazobenzene, not more than 100 parts per billion.
1,3-Diphenyltriazene, not more than 125 parts per billion.
4-Aminobiphenyl, not more than 275 parts per billion.
Azobenzene, not more than 1 part per million.
Benzidine, not more than 20 parts per billion.
Lead (as Pb), not more than 20 parts per million.
Arsenic (as As), not more than 3 parts per million.
Mercury (as Hg), not more than 1 part per million.
Total color, not less than 82 percent.

Sec. 74.1334 D&C Red No. 34.

(a) Identity. (1) The color additive D&C Red No. 34 is principally the calcium salt of 3-hydroxy-4-[(1-sulfo-2-naphthalenyl)azo]-2-naphthalene-carboxylic acid.

(2) Color additive mixtures for drug use made with D&C Red No. 34 may contain only those diluents that are suitable and that are listed in part 73 of this chapter as safe for use in color additive mixtures for coloring externally applied drugs.

(b) Specifications. D&C Red No. 34 shall conform to the following specifications and shall be free from impurities, other than those named, to the extent that such other impurities may be avoided by good manufacturing practice:

Sum of volatile matter (at 135° C.) and chlorides and sulfates (calculated at sodium salts), not more than 15 percent.

2-Amino-1-naphthalenesulfonic acid, calcium salt, not more than 0.2 percent.
3-Hydroxy-2-naphthoic acid, not more than 0.4 percent.
Subsidiary colors, not more than 4 percent.
Lead (as Pb), not more than 20 parts per million.
Arsenic (as As), not more than 3 parts per million.
Mercury (as Hg), not more than 1 part per million.
Total color not less than 85 percent.

Sec. 74.1336 D&C Red No. 36.

(a) Identity. (1) The color additive D&C Red No. 36 is 1-[(2-chloro-4-nitrophenyl)azo]-2-naphthalenol (CAS Reg. No. 2814-77-9). The color additive is manufactured by diazotization of 2-chloro-4-nitrobenzenamine in acid medium and coupling with 2-naphthalenol in acid medium.

(2) Color additive mixtures for drug use made with D&C Red No. 36 may contain only those diluents that are suitable and that are listed in part 73 of this chapter as safe for use in color additive mixtures for coloring drugs.

(b) Specifications. D&C Red No. 36 shall conform to the following specifications and shall be free from impurities other than those named to the extent that such impurities may be avoided by current good manufacturing practice:

Volatile matter at 135° C. (275° F.), not more than 1.5 percent.
Matter insoluble in toluene, not more than 1.5 percent.
2-Chloro-4-nitrobenzenamine, not more than 0.3 percent.
2-Naphthalenol, not more than 1 percent.
2,4-Dinitrobenzenamine, not more than 0.02 percent.
1-[(2,4-Dinitrophenyl)azo]-2-naphthalenol, not more than 0.5 percent.
4-[(2-Chloro-4-nitrophenyl)azo]-1-naphthalenol, not more than 0.5 percent.
1-[(4-Nitrophenyl)azo]-2-naphthalenol, not more than 0.3 percent.
1-[(4-Chloro-2-nitrophenyl)azo]-2-naphthalenol, not more than 0.3 percent.
Lead (as Pb), not more than 20 parts per million.
Arsenic (as As), not more than 3 parts per million.
Mercury (as Hg), not more than 1 part per million.
Total color, not less than 95 percent.

Sec. 74.1339 D&C Red No. 39.

(a) Identity. (1) The color additive D&C Red No. 39 is o-[p(β,β'-dihydroxy-diethylamino)-phenylazo]-benzoic acid.

(2) Color additive mixtures made with D&C Red No. 39 may contain the following diluents: Water, acetone, isopropyl alcohol, and specially denatured alcohols used in accordance with 26 CFR part 212.

(b) Specifications. D&C Red No. 39 shall conform to the following specifications and shall be free from impurities other than those named to the extent that such other impurities may be avoided by good manufacturing practice:

Volatile matter (at 100° C.), not more than 2.0 percent.
Matter insoluble in acetone, not more than 1.0 percent.
Anthranilic acid, not more than 0.2 percent.
N,N-(β,β'-Dihydroxy-diethyl) aniline, not more than 0.2 percent.

Subsidiary colors, not more than 3.0 percent.

Lead (as Pb), not more than 20 parts per million.

Arsenic (as As), not more than 3 parts per million.

Total color, not less than 95.0 percent.

Sec. 74.1340 FD&C Red No. 40.

(a) Identity and specifications. (1) The color additive FD&C Red No. 40 shall conform in identity and specifications to the requirements of § 74.340(a)(1) and (b).

(2) Color additive mixtures for drug use made with FD&C Red No. 40 may contain only those diluents that are suitable and that are listed in part 73 of this chapter as safe for use in color additive mixtures for coloring drugs.

(3) The listing of this color additive includes lakes prepared as described in §§ 82.51 and 82.1051 of this chapter, except that the color additive used is FD&C Red No. 40 and the resultant lakes meet the specification and labeling requirements prescribed by §§ 82.51 or 82.1051 of this chapter.)

(b) Uses and restrictions. (1) FD&C Red No. 40 and FD&C Red No. 40 Aluminum Lake may be safely used in coloring drugs, including those intended for use in the area of the eye, subject to the restrictions on the use of color additives in § 70.5(b) and (c) of this chapter, in amounts consistent with current good manufacturing practice.

(2) Other lakes of FD&C Red No. 40 may be safely used in coloring drugs, subject to the restrictions on the use of color additives in § 70.5 of this chapter, in amounts consistent with current good manufacturing practice.

Sec. 74.1602 D&C Violet No. 2.

(a) Identity. (1) The color additive D&C Violet No. 2 is principally 1-hydroxy-4-[(4-methylphenyl)amino]-9,10-anthracenedione.

(2) Color additive mixtures for use in externally applied drugs made with D&C Violet No. 2 may contain only those diluents that are suitable and that are listed in part 73 of this chapter as safe for use in color additive mixtures for coloring externally applied drugs.

(b) Specifications. D&C Violet No. 2 shall conform to the following specifications and shall be free from impurities, other than those named, to the extent that such other impurities can be avoided by good manufacturing practice:

Volatile matter (at 135° C.), not more than 2.0 percent.

Matter insoluble in both carbon tetrachloride and water, not more than 0.5 percent.

p-Toluidine, not more than 0.2 percent.

1-Hydroxy-9,10-anthracenedione, not more than 0.5 percent.

1,4-Dihydroxy-9,10-anthracenedione, not more than 0.5 percent.

Subsidiary colors, not more than 1.0 percent.

Lead (as Pb), not more than 20 parts per million.

Arsenic (as As), not more than 3 parts per million.

Total color, not less than 96.0 percent.

Sec. 74.1705 FD&C Yellow No. 5.

(a) Identity and specifications. (1) The color additive FD&C Yellow No. 5 shall conform in identity and specifications to the requirements of § 74.705 (a)(1) and (b).

(2) FD&C Yellow No. 5 Aluminum Lake shall be prepared in accordance with the requirements of § 82.51 of this chapter.

(3) Color additive mixtures for drug use made with FD&C Yellow No. 5 may contain only those diluents that are suitable and are listed in part 73 of this chapter as safe for use in color additive mixtures for coloring drugs.

(b) Uses and restrictions. (1) FD&C Yellow No. 5 may be safely used for coloring drugs generally, including drugs intended for use in the area of the eye, in amounts consistent with current good manufacturing practice.

(2) FD&C Yellow No. 5 Aluminum Lake may be safely used for coloring drugs intended for use in the area of the eye, when prepared in accordance with § 82.51 of this chapter.

Sec. 74.1706 FD&C Yellow No. 6.

(a) Identity and specifications. (1) The color additive FD&C Yellow No. 6 shall conform in identity and specifications to the requirements of § 74.706(a)(1) and (b).

(2) Color additive mixtures for drug use made with FD&C Yellow No. 6 may contain only those diluents that are suitable and that are listed in part 73 of this chapter as safe for use in color additive mixtures for coloring drugs.

(b) Uses and restrictions. FD&C Yellow No. 6 may be safely used for coloring drugs generally in amounts consistent with current good manufacturing practice.

Sec. 74.1707 D&C Yellow No. 7.

(a) Identity. (1) The color additive D&C Yellow No. 7 is principally fluorescein.

(2) Color additive mixtures for use in externally applied drugs made with D&C Yellow No. 7 may contain only those diluents that are suitable and that are listed in part 73 of this chapter for use in color additive mixtures for coloring externally applied drugs.

(b) Specifications. D&C Yellow No. 7 shall conform to the following specifications and shall be free from impurities other than those named to the extent that such impurities may be avoided by good manufacturing practice:

Sum of water and chlorides and sulfates (calculated as sodium salts), not more than 6 percent.

Matter insoluble in alkaline water, not more than 0.5 percent.

Resorcinol, not more than 0.5 percent.

Phthalic acid, not more than 0.5 percent.

2-2,4-(Dihydroxybenzoyl)benzoic acid, not more than 0.5 percent.

Lead (as Pb), not more than 20 parts per million.

Arsenic (as As), not more than 3 parts per million.

Mercury (as Hg), not more than 1 part per million.

Total color, not less than 94 percent.

Sec. 74.1707a Ext. D&C Yellow No. 7.

(a) Identity. (1) The color additive Ext. D&C Yellow No. 7 is principally the disodium salt of 8-hydroxy-5,7-di-nitro-2-naphthalenesulfonic acid.

(2) Color additive mixtures for drug use made with Ext. D&C Yellow No. 7 may contain only those diluents that are suitable and that are listed in part 73 of this chapter as safe for use in color additive mixtures for coloring externally applied drugs.

(b) Specifications. Ext. D&C Yellow No. 7 shall conform to the following specifications and shall be free from impurities, other than those named, to the extent that such other impurities may be avoided by good manufacturing practice:

Sum of volatile matter (at 135° C.) and chlorides and sulfates (calculated as sodium salts), not more than 15 percent.

Water-insoluble matter, not more than 0.2 percent.

1-Naphthol, not more than 0.2 percent.

2,4-Dinitro-1-naphthol, not more than 0.03 percent.

Lead (as Pb), not more than 20 parts per million.

Arsenic (as As), not more than 3 parts per million.

Mercury (as Hg), not more than 1 part per million.

Total color, not less than 85 percent.

Sec. 74.1708 D&C Yellow No. 8.

(a) Identity. (1) The color additive D&C Yellow No. 8 is principally the disodium salt of fluorescein.

(2) Color additive mixtures for use in externally applied drugs made with D&C Yellow No. 8 may contain only those diluents that are suitable and that are listed in part 73 of this chapter for use in color additive mixtures for coloring externally applied drugs.

(b) Specifications. D&C Yellow No. 8 shall be free from impurities other than those named to the extent that such impurities may be avoided by good manufacturing practice:

Sum of water and chlorides and sulfates (calculated as sodium salts), not more than 15 percent.

Matter insoluble in alkaline water, not more than 0.3 percent.

Resorcinol, not more than 0.5 percent.

Phthalic acid, not more than 1 percent.

2-(2,4-Dihydroxybenzoyl)benzoic acid, not more than 0.5 percent.

Lead (as Pb), not more than 20 parts per million.

Arsenic (as As), not more than 3 parts per million.

Mercury (as Hg), not more than 1 part per million.

Total color, not less than 85 percent.

Sec. 74.1710 D&C Yellow No. 10.

(a) Identity. (1) The color additive D&C Yellow No. 10 is a mixture of the sodium salts of the mono- and disulfonic acids of 2-(2-quinolinyl)-1H-indene-1,3 (2H)-dione consisting principally of the sodium salts of 2-(2,3-dihydro-1,3-dioxo-1H-indene-2-yl)-6-quinolinesulfonic acid and 2-(2,3-dihydro-1,3-dioxo-1H-indene-2-yl)-8-quinolinesulfonic acid with lesser amounts of the disodium salts of the disulfonic acids of 2-(2-quinolinyl)-1H-indene-1,3(2H)-dione (CAS Reg. No. 8004-92-0). D&C Yellow No. 10 is manufactured by condensing quinaldine with phthalic anhydride to give the unsulfonated dye, which is then sulfonated with oleum.

(2) Color additive mixtures made with D&C Yellow No. 10 for drug use may contain only those diluents that are suitable and that are listed in part 73 of this chapter as safe for use in color additive mixtures for coloring drugs.

(b) Specifications. The color additive D&C Yellow No. 10 shall conform to the following specifications and shall be free from impurities other than those named to the extent that such other impurities may be avoided by current good manufacturing practice:

Sum of volatile matter at 135° C. (275° F.) and chlorides and sulfates (calculated as sodium salts), not more than 15 percent.

Matter insoluble in both water and chloroform, not more than 0.2 percent.

Total sulfonated quinaldines, sodium salts, not more than 0.2 percent.

Total sulfonated phthalic acids, sodium salts, not more than 0.2 percent.

2-(2-Quinolinyl)-1H-indene-1,3 (2H)-dione, not more than 4 parts per million.

Sum of sodium salts of the monosulfonates of 2-(2-quinolinyl)-1H-indene-1,3 (2H)-dione, not less than 75 percent.

Sum of sodium salts of the disulfonates of 2-(2-quinolinyl)-1H-indene-1,3 (2H)-dione, not more than 15 percent.

2-(2,3-Dihydro-1,3-dioxo-1H-indene-2-yl)-6,8-quinolinedisulfonic acid, disodium salt, not more than 3 percent.

Diethyl ether soluble matter other than that specified, not more than 2 parts per million, using added 2-(2-quinolinyl)-1H-indene-1,3 (2H)-dione for calibration.

Lead (as Pb), not more than 20 parts per million.

Arsenic (as As), not more than 3 parts per million.

Mercury (as Hg), not more than 1 part per million.

Total color, not less than 85 percent.

Sec. 74.1711 D&C Yellow No. 11.

(a) Identity. (1) The color additive D&C Yellow No. 11 is principally 2-(2-quinolyl)-1,3-indandione.

(2) Color additive mixtures, for drug use made with D&C Yellow No. 11 may contain only those diluents that are suitable and that are listed in part 73 of this chapter as safe for use in color additive mixtures for coloring externally applied drugs.

(b) Specifications. D&C Yellow No. 11 shall conform to the following specifications and shall be free from impurities, other than those named, to the extent that such other impurities may be avoided by good manufacturing practice:

Volatile matter (at 135° C.), not more than 1 percent.

Ethyl alcohol-insoluble matter, not more than 0.4 percent.

Phthalic acid, not more than 0.3 percent.

Quinaldine, not more than 0.2 percent.

Subsidiary colors, not more than 5 percent.

Lead (as Pb), not more than 20 parts per million.

Arsenic (as As), not more than 3 parts per million.

Mercury (as Hg), not more than 1 part per million.

Total color, not less than 96 percent.

Sec. 74.2101 FD&C Blue No. 1.

(a) Identity. The color additive FD&C Blue No. 1 is principally the disodium salt of ethyl[4-[p-[ethyl(m-sulfobenzyl)amino]-α-(o-sulfophenyl)benzylidene]-2,5-cyclohexadien-1-ylidene](m-sulfobenzyl)ammonium hydroxide inner salt with smaller amounts of the isomeric disodium salts of ethyl[4-[p-[ethyl(p-sulfobenzyl)amino]-α-(o-sulfophenyl)benzylidene]-2,5-cyclohexadien-1-ylidene](p-sulfobenzyl)ammonium hydroxide inner salt and ethyl[4-[p-[ethyl(o-sulfobenzyl)amino]-α-(o-sulfophenyl)benzylidene]-2,5-cyclohexadien-1-ylidene](o-sulfobenzyl)ammonium hydroxide inner salt. Additionally, FD&C Blue No. 1 is manufactured by the acid catalyzed condensation of one mole of sodium 2-formylbenzenesulfonate with two moles from a mixture consisting principally of 3-[(ethylphenylamino)methyl]benzenesulfonic acid, and smaller amounts of 4-[(ethylphenylamino)methyl]benzenesulfonic acid and 2-[(ethylphenylamino)methyl]benzenesulfonic acid to form the leuco base. The leuco base is then oxidized with lead dioxide and acid, or with dichromate and acid, or with manganese dioxide and acid to form the dye. The intermediate sodium 2-formylbenzenesulfonate is prepared from 2-chlorobenzaldehyde and sodium sulfite.

(b) Specifications. (1) The color additive FD&C Blue No. 1 shall conform in specifications to the requirements of § 74.101(b).

(2) FD&C Blue No. 1 Aluminum Lake shall be prepared in accordance with the requirements of § 82.51 of this chapter.

Sec. 74.2151 D&C Brown No. 1.

(a) Identity. The color additive D&C Brown No. 1 is a mixture of the sodium salts of 4[[5-[(dialkylphenyl)-azo]-2,4-dihydroxyphenyl]azo]-benzene sulfonic acid. The alkyl group is principally the methyl group.

(b) Specifications. D&C Brown No. 1 shall conform to the following specifications and shall be free from impurities other than those named to the extent that such other impurities may be avoided by good manufacturing practice:

Sum of volatile matter (at 135° C.) and chlorides and sulfates (calculated as sodium salts), not more than 16 percent.

Water-insoluble matter, not more than 0.2 percent.

Sulfanilic acid, sodium salt, not more than 0.2 percent.

Resorcinol, not more than 0.2 percent.

Xylidines, not more than 0.2 percent.

Disodium salt of 4[[5-[(4-sulfophenyl)-azo]-2,4-dihydroxyphenyl]azo]benzenesulfonic acid, not more than 3 percent.

Monosodium salt of 4[[5-[(2,4-dimethyl-phenyl)azo]-2,4-dihydroxyphenyl]azo]benzenesulfonic acid, not less than 29 percent and not more than 39 percent.

Monosodium salt of 4[[5-[(2,5-dimethyl-phenyl)azo]-2,4-dihydroxyphenyl]azo]benzenesulfonic acid, not less than 12 percent and not more than 17 percent.

Monosodium salt of 4[[5-[(2,3-dimethyl-phenyl)azo]-2,4-dihydroxyphenyl]azo]benzenesulfonic acid, not less than 6 percent and not more than 13 percent.

Monosodium salt of 4[[5-[(2-ethylphenyl)-azo]-2,4-dihydroxyphenyl]-azo]benzenesulfonic acid, not less than 5 percent and not more than 12 percent.

Monosodium salt of 4[[5-[(3,4-dimethyl-phenyl)azo]-2,4-dihydroxyphenyl]azo]benzenesulfonic acid, not less than 3 percent and not more than 9 percent.

Monosodium salt of 4[[5-[(2,6-dimethyl-phenyl)azo]-2,4-dihydroxyphenyl]azo]benzenesulfonic acid, not less than 3 percent and not more than 8 percent.

Monosodium salt of 4[[5-[(4-ethylphenyl) azo]-2,4-dihydroxyphenyl]-azo]benzenesulfonic acid, not less than 2 percent and not more than 8 percent.

Lead (as Pb), not more than 20 parts per million.
Arsenic (as As), not more than 3 parts per million.
Mercury (as Hg), not more than 1 part per million.
Total color, not less than 84 percent.
Sec. 74.2602a Ext. D&C Violet No. 2.

(a) Identity. The color additive Ext. D&C Violet No. 2 is principally the monosodium salt of 2-[(9,10-dihydro-4-hydroxy-9,10-dioxo-1-anthracenyl)amino]-5-methyl-benzenesulfonic acid.

(b) Specifications. Ext. D&C Violet No. 2 shall conform to the following specifications and shall be free from impurities, other than those named, to the extent that such other impurities may be avoided by good manufacturing practice:

Sum of volatile matter (at 135° C.) and chlorides and sulfates (calculated as sodium salts), not more than 18 percent.

Water-insoluble matter, not more than 0.4 percent.
1-Hydroxy-9,10-anthracenedione, not more than 0.2 percent.
1,4-Dihydroxy-9,10-anthracenedione, not more than 0.2 percent.
p-Toluidine, not more than 0.1 percent.
p-Toluidine sulfonic acids, sodium salts, not more than 0.2 percent.
Subsidiary colors, not more than 1 percent.
Lead (as Pb), not more than 20 parts per million.
Arsenic (as As), not more than 3 parts per million.
Mercury (as Hg), not more than 1 part per million.
Total color, not less than 80 percent.
Sec. 74.2705 FD&C Yellow No. 5.

(a) Identity. The color additive FD&C Yellow No. 5 is principally the trisodium salt of 4,5-dihydro-5-oxo-(1-4-sulfophenyl)-4-[(4-sulfophenyl)azo]-1H-pyrazole-3-carboxylic acid (CAS Reg. No. 1934-21-0). To manufacture the additive, 4-aminobenzenesulfonic acid is diazotized using hydrochloric acid and sodium nitrite. The diazo compound is coupled with 4,5-dihydro-5-oxo-1-(4-sulfophenyl)-1H-pyrazole-3-carboxylic acid or with the methyl ester, the ethyl ester, or a salt of this carboxylic acid. The resulting dye is purified and isolated as the sodium salt.

(b) Specifications. (1) FD&C Yellow No. 5 shall conform to the following specifications and shall be free from impurities other than those named to the extent that such other impurities may be avoided by good manufacturing practice:

Sum of volatile matter at 135° C. (275° F.) and chlorides and sulfates (calculated as sodium salts), not more than 13 percent.

Water-insoluble matter, not more than 0.2 percent.
4,4'-[4,5-Dihydro-5-oxo-4-[(4-sulfophenyl)hydrazono]-1H-pyrazol-1,3-diyl]bis[benzenesulfonic acid], trisodium salt, not more than 1 percent.

4-[(4',5-Disulfo[1,1'-biphenyl]-2-yl)hydrazono]-4,5-dihydro-5-oxo-1-(4-sulfophenyl-1H-pyrazole-3-carboxylic acid, tetrasodium salt, not more than 1 percent.

Ethyl or methyl 4,5-dihydro-5-oxo-1-(4-sulfophenyl)-4-[(4-sulfophenyl)hydrazono]-1H-pyrazole-3-carboxylate, disodium salt, not more than 1 percent.

Sum of 4,5-dihydro-5-oxo-1-phenyl-4-[(4-sulfophenyl)azo]-1H-pyrazole-3-carboxylic acid, disodium salt, and 4,5-dihydro-5-oxo-4-(phenylazo)-1-(4-sulfophenyl)-1H-pyrazole-3-carboxylic acid, disodium salt, not more than 0.5 percent.

4-Aminobenzenesulfonic acid, sodium salt, not more than 0.2 percent.

4,5-Dihydro-5-oxo-1-(4-sulfophenyl)-1H-pyrazole-3-carboxylic acid, disodium salt, not more than 0.2 percent.

Ethyl or methyl 4,5-dihydro-5-oxo-1-(4-sulfophenyl)-1H-pyrazole-3-carboxylate, sodium salt, not more than 0.1 percent.

4,4'-(1-Triazene-1,3-diyl)bis[benzenesulfonic acid], disodium salt, not more than 0.05 percent.

4-Aminoazobenzene, not more than 75 parts per billion.
4-Aminobiphenyl, not more than 5 parts per billion.
Aniline, not more than 100 parts per billion.
Azobenzene, not more than 40 parts per billion.
Benzidine, not more than 1 part per billion.
1,3-Diphenyltriazene, not more than 40 parts per billion.
Lead (as Pb), not more than 10 parts per million.
Arsenic (as As), not more than 3 parts per million.
Mercury (as Hg), not more than 1 part per million.
Total color, not less than 87 percent.

(2) FD&C Yellow No. 5 Aluminum Lake shall be prepared in accordance with the requirements of § 82.51 of this chapter.

Sec. 74.3045 [Phthalocyaninato(2-)]copper.

(a) Identity. The color additive is [phthalocyaninato(2-)]copper (CAS Reg. No. 147-14-8) having the structure shown in Colour Index No. 74160.

(b) Specifications. The color additive [phthalocyaninato(2-)]copper shall conform to the following specifications and shall be free from impurities other than those named to the extent that such impurities may be avoided by current good manufacturing practice:

Volatile matter 135° C. (275° F.), not more than 0.3 percent.
Salt content (as NaCl), not more than 0.3 percent.
Alcohol soluble matter, not more than 0.5 percent.
Organic chlorine, not more than 0.5 percent.
Aromatic amines, not more than 0.05 percent.
Lead (as Pb), not more than 40 parts per million.
Arsenic (as As), not more than 3 parts per million.
Mercury (as Hg), not more than 1 part per million.
Total color, not less than 98.5 percent.
Sec. 74.3106 D&C Blue No. 6.

(a) Identity. The color additive D&C Blue No. 6 is principally [Δ2,2'-biindoline]-3,3'dione (CAS Reg. No. 482-89-3).

(b) Specifications. D&C Blue No. 6 shall conform to the following specifications and shall be free from impurities other than those named to the extent that such impurities may be avoided by good manufacturing practice:

Volatile matter at 135° C. (275° F.), not more than 3 percent.

Matter insoluble in N,N-dimethylformamide, not more than 1 percent.

Isatin, not more than 0.3 percent.

Anthranilic acid, not more than 0.3 percent.

Indirubin, not more than 1 percent.

Lead (as Pb), not more than 10 parts per million.

Arsenic (as As), not more than 3 parts per million.

Mercury (as Hg), not more than 1 part per million.

Total color, not less than 95 percent.

What is claimed is:

1. A hair dye composition comprising one or more dyes, a liquid vehicle, and a styrene/vinylpyrrolidone copolymer emulsion, wherein said dyes are selected from the group consisting of cationic dyes, anionic dyes, and solvent dyes.

2. The hair dye composition of claim 1, wherein said styrene/vinylpyrrolidone copolymer emulsion is present in an amount less than about 20% by weight.

3. A hair dye composition comprising one or more dyes, a liqiuid vehicle, a styrene/vinylpyrrolidone copolymer emulsion, and a copolymer of vinyl acetate and vinyl pyrrolidone.

4. A hair dye composition comprising one or more dyes, a liquid vehicle, and a styrene/vinylpyrrolidone copolymer emulsion, wherein said liquid vehicle comprises at least one alcohol.

5. A conditioner comprising cationic holding polymer, cationic wheat protein, cationic conditioning agent, cationic cellulosic polymer, silicone, and glycerin.

6. The conditioner of claim 5, further comprising an ultraviolet light protector.

7. The conditioner of claim 5, further comprising at least one extract.

8. The conditioner of claim 7, wherein said at least one extract is selected from the group consisting of chamomile extract, lemon extract, rosehips extract, and green tea extract.

9. The conditioner of claim 5, wherein said cationic holding polymer is a quaternized copolymer of vinylpyrrolidone and dimethylaminoethyl methacrylate.

10. The conditioner of claim 5, wherein said cationic wheat protein is a hydrolyzed wheat protein.

11. The conditioner of claim 5, wherein said cationic conditioning agent is olealkonium chloride.

12. A combination leave-in conditioner and hair dye composition, comprising:

(a) at least one hair dye;

(b) cationic holding polymer;

(c) cationic wheat protein;

(d) cationic conditioning agent;

(e) cationic cellulosic polymer;

(f) a styrene/vinylpyrrolidone copolymer emulsion; and (g) glycerin.

13. The composition of claim 12, further comprising a copolymer of vinyl acetate and vinyl pyrrolidone.

14. The composition of claim 12, further comprising silicone.

15. The composition of claim 12, further comprising amodimethicone.

16. The composition of claim 12, wherein said hair dye comprises at least one member selected from the group consisting of azo dye, cationic dye, diphenyldiamine dye, quinone-imine dye containing a quaternary ammonium group, and direct nitro dye.

* * * * *